United States Patent
Guo

(10) Patent No.: US 9,759,689 B2
(45) Date of Patent: Sep. 12, 2017

(54) REAL-TIME DETECTION AND IMAGING OF TERAHERTZ PULSE RADIATION BY USING PHOTOACOUSTIC CONVERSION

(71) Applicant: THE REGENTS OF THE UNIVERSITY OF MICHIGAN, Ann Arbor, MI (US)

(72) Inventor: Lingjie Jay Guo, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 102 days.

(21) Appl. No.: 14/701,806

(22) Filed: May 1, 2015

(65) Prior Publication Data

US 2015/0316511 A1 Nov. 5, 2015

Related U.S. Application Data

(60) Provisional application No. 61/987,849, filed on May 2, 2014.

(51) Int. Cl.
| | |
|---|---|
| *H04B 10/00* | (2013.01) |
| *G01N 29/24* | (2006.01) |
| *H04B 10/27* | (2013.01) |
| *G01N 29/22* | (2006.01) |
| *H04B 10/90* | (2013.01) |

(52) U.S. Cl.
CPC ....... *G01N 29/2418* (2013.01); *G01N 29/221* (2013.01); *H04B 10/27* (2013.01); *H04B 10/90* (2013.01); *G01N 2291/028* (2013.01); *G01N 2291/101* (2013.01)

(58) Field of Classification Search
CPC ............. G01N 29/2418; G01N 29/221; G01N 2291/028; G01N 2291/101; H04B 10/27

USPC ......................................................... 398/140
See application file for complete search history.

(56) References Cited

U.S. PATENT DOCUMENTS

| | | | |
|---|---|---|---|
| 8,946,683 B2* | 2/2015 | Rogers ................... | B82Y 10/00 257/40 |
| 2013/0153790 A1* | 6/2013 | Clough .............. | G01N 21/3581 250/473.1 |
| 2013/0182620 A1* | 7/2013 | Chaffee .............. | H04B 10/1121 370/310 |

OTHER PUBLICATIONS

Liu, "Enhancement of photoacoustic emission through terahertz-field-driven electron motions," Physical Review, E 82, 066602 2010, Dec. 13, 2010.*
Clough, "Encoding terahertz signatures into laser-induced plasma acoustic waves," Proc. of SPIE, vol. 7938, 793804, 2011.*
Delmerche, "Stability of Molded Polydimethylsiloxane Microstructures," 1997 Adv. Mat. 9:741-746.*

(Continued)

*Primary Examiner* — Juan A Torres
(74) *Attorney, Agent, or Firm* — Harness, Dickey & Pierce, P.L.C.

(57) ABSTRACT

Methods and devices for high speed detection of terahertz radiation are provided. A photoacoustic transducer receives a pulse of terahertz (THz) radiation. The transducer may comprise a solid, liquid, or semi-solid material. For example, the transducer may be a composite material having a polymer and radiation absorbing particles. The photoacoustic transducer produces an acoustic wave (e.g., an ultrasound wave) in response to receiving the pulse of THz radiation. An acoustic sensor receives the acoustic wave produced by the photoacoustic transducer and thus provides detection of the THz wave.

21 Claims, 12 Drawing Sheets

(56) References Cited

OTHER PUBLICATIONS

Ling, et al., "High-sensitivity and wide-directivity ultrasound detection using high Q polymer micro-ring resonators," App. Phys. Lett. 98, pp. 204103-1-204103-3 (2011).
Maxwell, et al., "Polymer microring resonators for high-frequency ultrasound detection and imaging," IEEE J. Sel. Top. Quantum. Electron. 14(1), pp. 191-197 (Jan./Feb. 2008).
Chao, et al., "High-frequency ultrasound sensors using polymer microring resonators," IEEE Trans. Ultrason. Ferroelect. Freq. Contr. 54(5), pp. 957-965 (May 2007).
Hsieh, et al., "All-optical scanhead for ultrasound and photoacoustic dual-modality imaging," Opt. Express 20(2), pp. 1588-1596 (Jan. 16, 2012).
Clough, et al., "Laser-induced photoacoustics influenced by single-cycle terahertz radiation," Opt. Lett., 35(20), pp. 3544-3546 (Nov. 1, 2010).
Chen, et al., "Low-noise small-size microring ultrasonic detectors for high-resolution photoacoustic imaging," J. Biomed. Opt., 16(5), pp. 056001-1-056001-6 (May 2011).
Baac, et al., "Carbon-Nanotube Optoacoustic Lens for Focused Ultrasound Generation and High-Precision Targeted Therapy," Scientific Reports, 2, 989; DOI: 10.1038/srep0098, pp. 1-8 (2012).
Glauvitz, et al., "A MEMS Photoacoustic Detector of Terahertz Radiation for Chemical Sensing," Procedia Engineering. 47. pp. 730-733 (2012).
Chen, "Optical Microrign Resonators for Photoacoustic Imaging and Detection", University of Michigan, Ann Arbor Michigan, http://mirlyn.lib.umich.edu/Record/011662157, 150 pages (2012).

\* cited by examiner

REAL-TIME DETECTION AND IMAGING OF TERAHERTZ PULSE RADIATION BY USING PHOTOACOUSTIC CONVERSION

CROSS-REFERENCE TO RELATED APPLICATIONS

This application claims priority U.S. Provisional Application No. 61/987,849, filed on May 2, 2014. The entire disclosure of this application is incorporated herein by reference.

GOVERNMENT RIGHTS

This invention is made with government support under DMR1120923 and DMR1120187 awarded by the National Science Foundation. The Government has certain rights in the invention.

FIELD

The present disclosure relates to methods, devices, and systems for detecting radiation, for example, terahertz radiation. In particular, the present disclosure pertains to methods, devices, and systems for real-time detection and imaging of terahertz pulse radiation by photoacoustic conversion and signal detection.

BACKGROUND

This section provides background information related to the present disclosure which is not necessarily prior art.

Radiation sensing, such as terahertz (THz) radiation sensing, can be applied in a variety of applications in industry, biology, and material science. Terahertz (THz) electromagnetic (EM) radiation waves fall on the electromagnetic spectrum between infrared radiation waves and microwaves, typically having a wavelength of greater than or equal to about 100 µm to less than or equal to about 1 mm with frequencies ranging from greater than or equal to about 0.1 THz to less than or equal to about 10 THz. THz radiation comprises a scientifically rich frequency band and offers unique value for imaging, chemical identification, and characterization of electronic and vibrational properties of materials. The low photon energies of THz radiation, e.g., 4 meV at 1 THz, are biologically safe, making it an attractive tool for non-ionizing radiation for imaging and treating biological tissues. Such non-destructive, non-radiation imaging is particularly desirable for medical imaging, chemical analysis, and security screening.

Thus, active and passive devices for THz radiation have been the subject of intense research. Most existing techniques for THz sensing either require bulky optics or need cryogenic cooling. Additionally, applications requiring fast detection in real time are limited due to long detector integration times (1-1000 ms). Development of small, rapid response, easy-to-operate THz components, including sources, waveguides, and detectors, would be highly advantageous. Indeed, better control and measurement of THz radiation is necessary to open up a range of potential uses and applications for THz radiation.

SUMMARY

This section provides a general summary of the disclosure, and is not a comprehensive disclosure of its full scope or all of its features.

In certain aspects, the present disclosure provides a device for detecting terahertz radiation. In certain aspects, the detection device comprises a photoacoustic transducer configured to receive a pulse of terahertz (THz) radiation. The photoacoustic transducer comprises a material that absorbs THz radiation and produces an acoustic wave in response to receiving the pulse of THz radiation. An acoustic sensor is provided that is configured to receive the acoustic wave produced by the photoacoustic transducer.

In certain other aspects, the present disclosure provides a device for detecting terahertz radiation comprising a photoacoustic transducer configured to receive a pulse of terahertz (THz) radiation. The photoacoustic transducer comprises a composite material having a polymeric matrix material and a plurality of radiation absorbing particles distributed in the polymeric matrix material. The photoacoustic transducer produces an acoustic wave in response to receiving the pulse of THz radiation. An acoustic sensor is provided that is configured to receive the acoustic wave produced by the photoacoustic transducer.

In other aspects, the present disclosure contemplates a method for detecting terahertz radiation. The method comprises generating an acoustic wave within a photoacoustic transducer by receiving a pulse of terahertz (THz) radiation. The photoacoustic transducer comprises a composite material having a polymeric matrix material and a plurality of radiation absorbing particles distributed in the polymeric matrix material. The method further comprises detecting the acoustic wave with an acoustic sensor. Such methods provide rapid detection of THz radiation, in some aspects, providing real-time detection.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figures 3A, 3B:
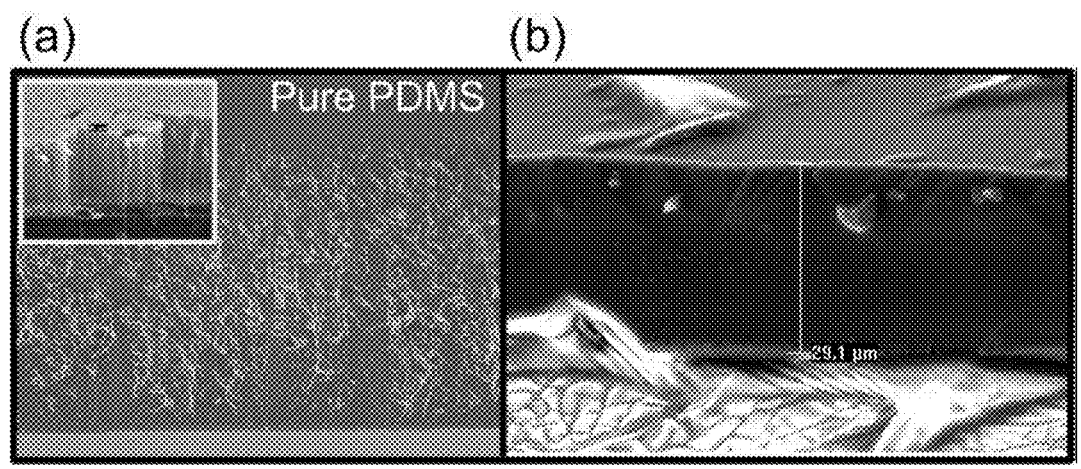

FIGS. 3(a)-3(b). SEM photographs of carbon nanotube and polydimethylsiloxane (CNT-PDMS) composite films prepared in accordance with certain aspects of the present disclosure. The composites are made with a thick spacer of 0.5 mm (FIG. 3(a)) and a thin spacer of 25 µm (FIG. 3(b)). In FIG. 3(a), the pure PDMS layer is too thick and thus is less suitable as a photoacoustic (PA) transmitter. The inset in FIG. 3(a) shows a CNT forest grown to have an average particle length of about 45 µm before PDMS infiltration. Compared with the visible nano scale texture of CNTs in FIG. 3(a), most CNTs are invisible in FIG. 3(b), because more PDMS encompasses the boundaries due to more pressing and infiltration.

Figure 4:
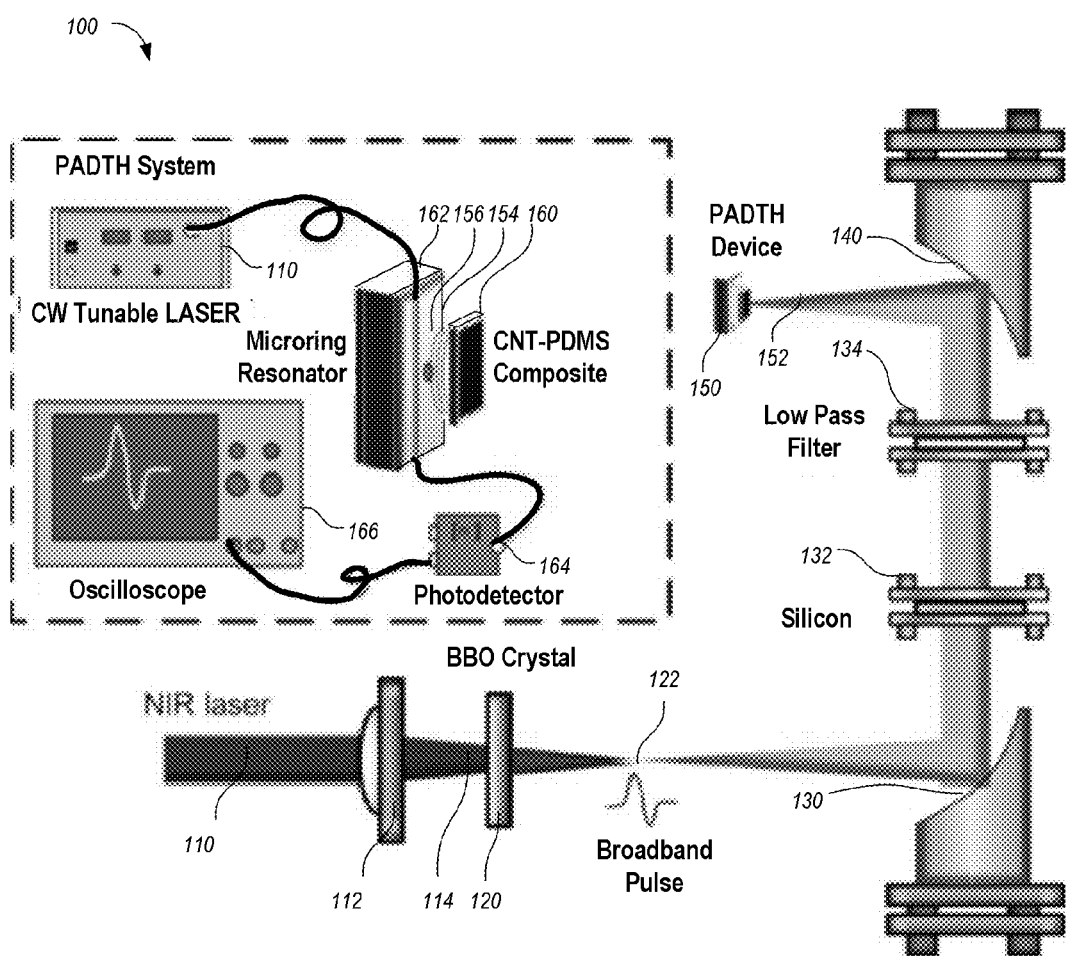

FIG. 4 shows an experimental setup for a system for photoacoustic detection of terahertz (THz) radiation (PADTH) and THz pulse generation in accordance with certain variations of the present disclosure. THz radiation is generated by mixing a fundamental pulse and its second-harmonic laser field produced from a BBO crystal. A broadband pulse is collected and collimated by a parabolic mirror and then a silicon wafer and a low-pass filter are used to select radiation frequencies less than 6 THz, which is then re-focused by a second parabolic mirror on a PADTH detection device. The detection device comprises a composite transducer formed of carbon nanotubes (CNT) and polydimethylsiloxane (PDMS) and an optical microring resonator. An ultrasonic gel is disposed between the transducer and microring resonator for sound coupling. A CW tunable laser and a high-speed photodetector are used to probe the acoustic pressure on the microring resonator.

Figures 5A, 5B, 5C, 5D:
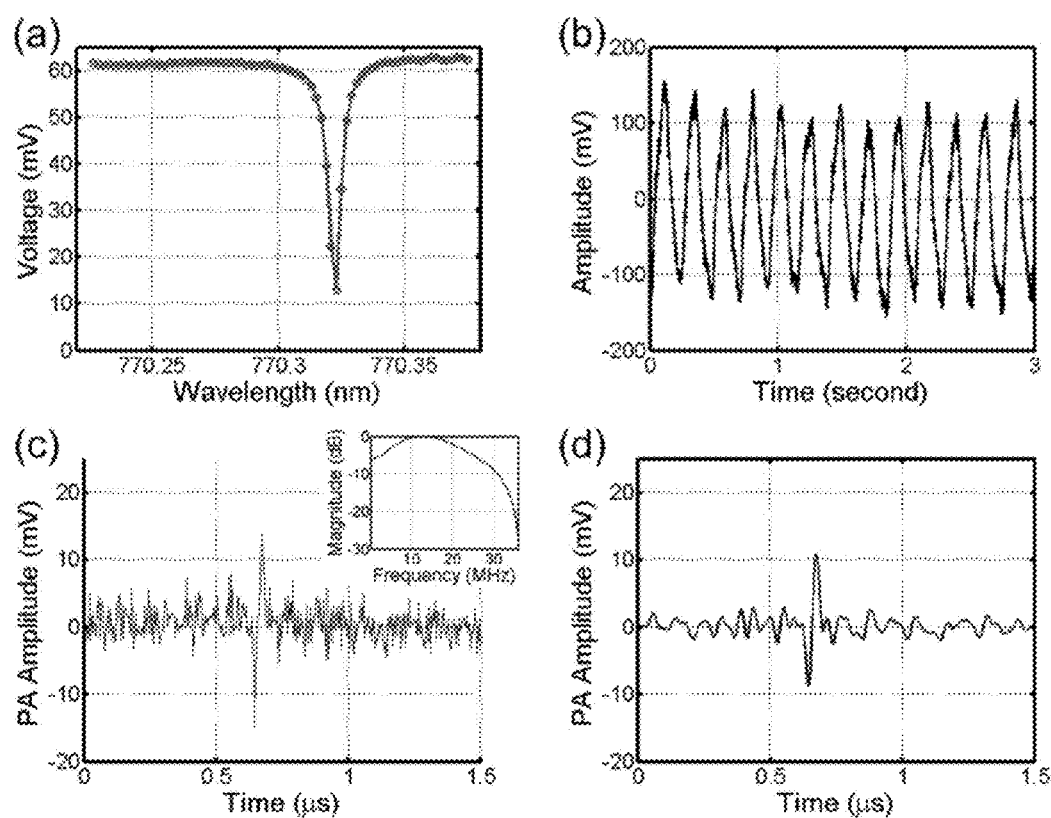

FIGS. 5(a)-5(d) show a THz-induced photoacoustic (PA) time-domain signal detected by microring ultrasonic detectors. FIG. 5(a) shows optical transmission spectrum of the polymer microring resonator. The resonance bandwidth is approximately 60 pm. FIG. 5(b) shows measured THz power by the pyroelectric detector at a modulation frequency of 5 Hz. FIG. 5(c) shows a single-shot PA waveform excited by one THz pulse with energy of 3.6 nJ. The SNR is 16.9 dB. The inset in FIG. 5(c) shows spectrum of THz pulse-excited PA waveform. FIG. 5(d) shows the PA signal of FIG. 5(c) after applying a matched filter (1-26 MHz). The improved SNR is 21.5 dB.

Figure 6:
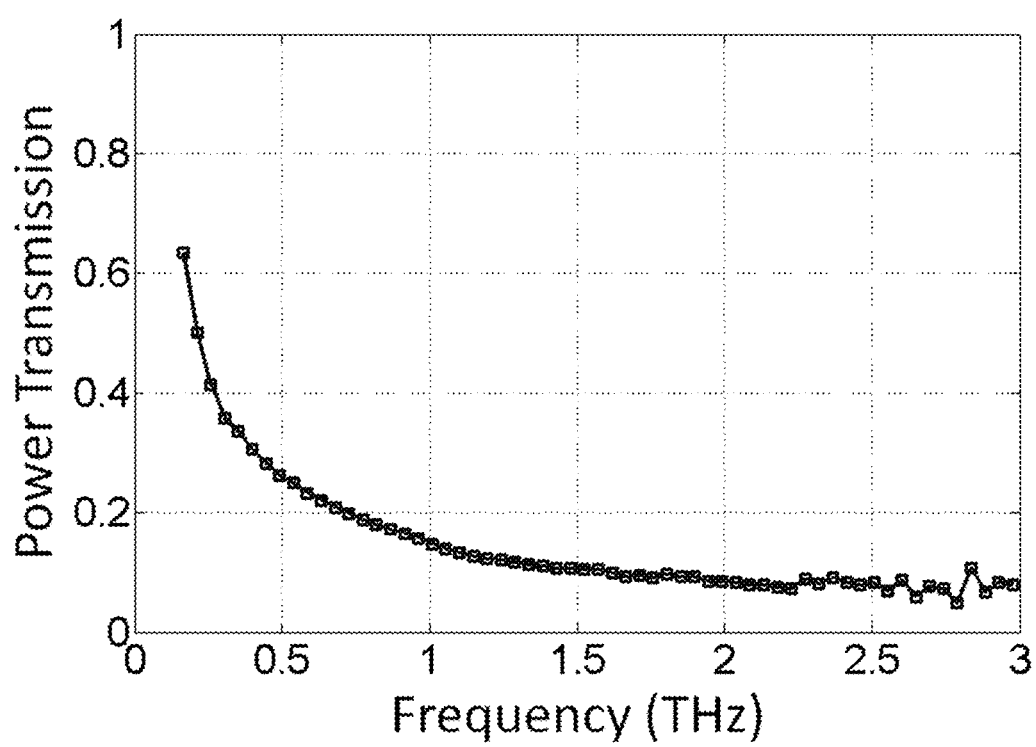

FIG. 6 shows power transmission spectrum of a composite transducer (power transmission versus frequency (THz)). The transmission spectrum of the CNT-PDMS composite (having a thickness of approximately 30 µm) at frequencies of 0.2-3 THz obtained using THz time-domain spectroscopy is shown.

Figure 7:
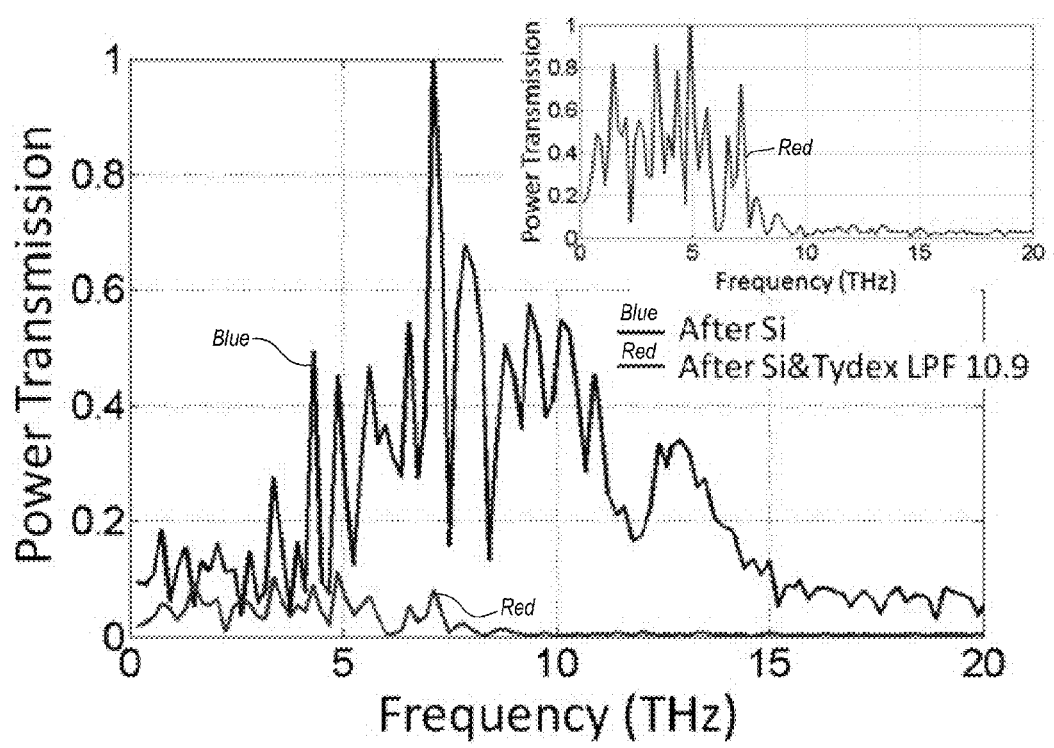

FIG. 7 shows spectra of produced THz pulse after silicon (Si) (blue) and after Si and a commercial low-pass filter (red), which has a cut-off frequency at 6 THz (the frequency at which the transmission is 50% of the maximum value). The normalized spectrum after the low-pass filter is shown in the inset for better display. The fine dips in the spectrum are due to the water vapor, which has many absorption lines at THz frequencies.

Figures 8A, 8B, 8C:
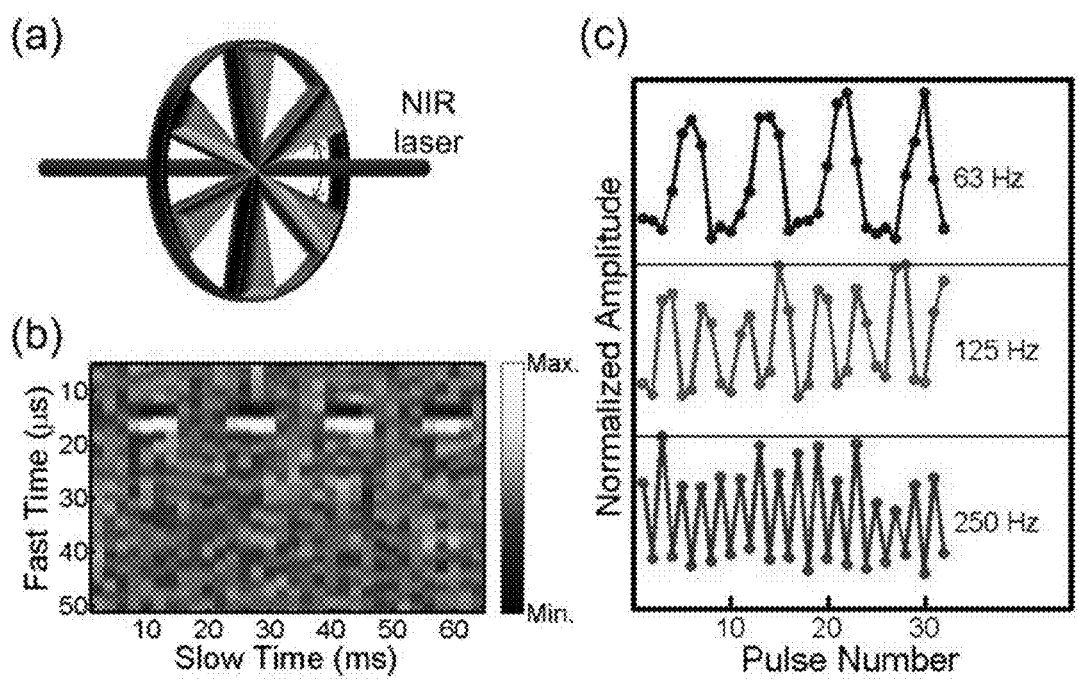

FIGS. 8(a)-8(c) demonstrate real-time detection of THz pulses via the detection systems according to certain aspects of the present disclosure. A mechanical chopper is placed before a focusing lens of the NIR laser. The chopper frequencies are set at 63 Hz, 125 Hz, and 250 Hz, respectively. FIG. 8(a) shows a schematic of NIR laser spot and the fan of the chopper. The length of the marked arc is approximately 10 mm. FIG. 8(b) shows recorded PA signals as a function of elapsed time at the chopper frequency of 63 Hz. FIG. 8(c) shows peak amplitude of the PA signal after Hilbert transform (envelope) as a function of each THz pulse. Results of 3 different designated frequencies of the chopper are plotted.

Figure 9:
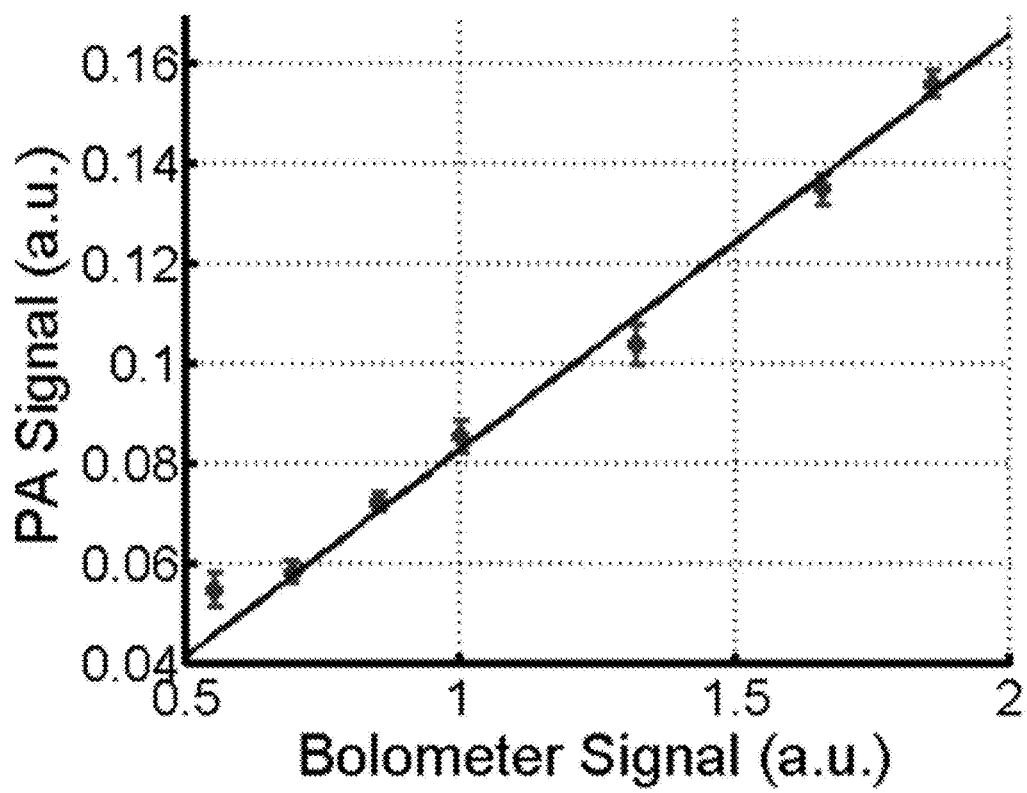

FIG. 9 shows characterization of linear response of a photoacoustic terahertz detector device (PADTH) according to certain aspects of the present disclosure. Characteristics of the measured PA signal amplitude by the PADTH method as a function of THz energy are shown, which is monitored by a bolometer.

Figures 10A, 10B, 10C, 10D:
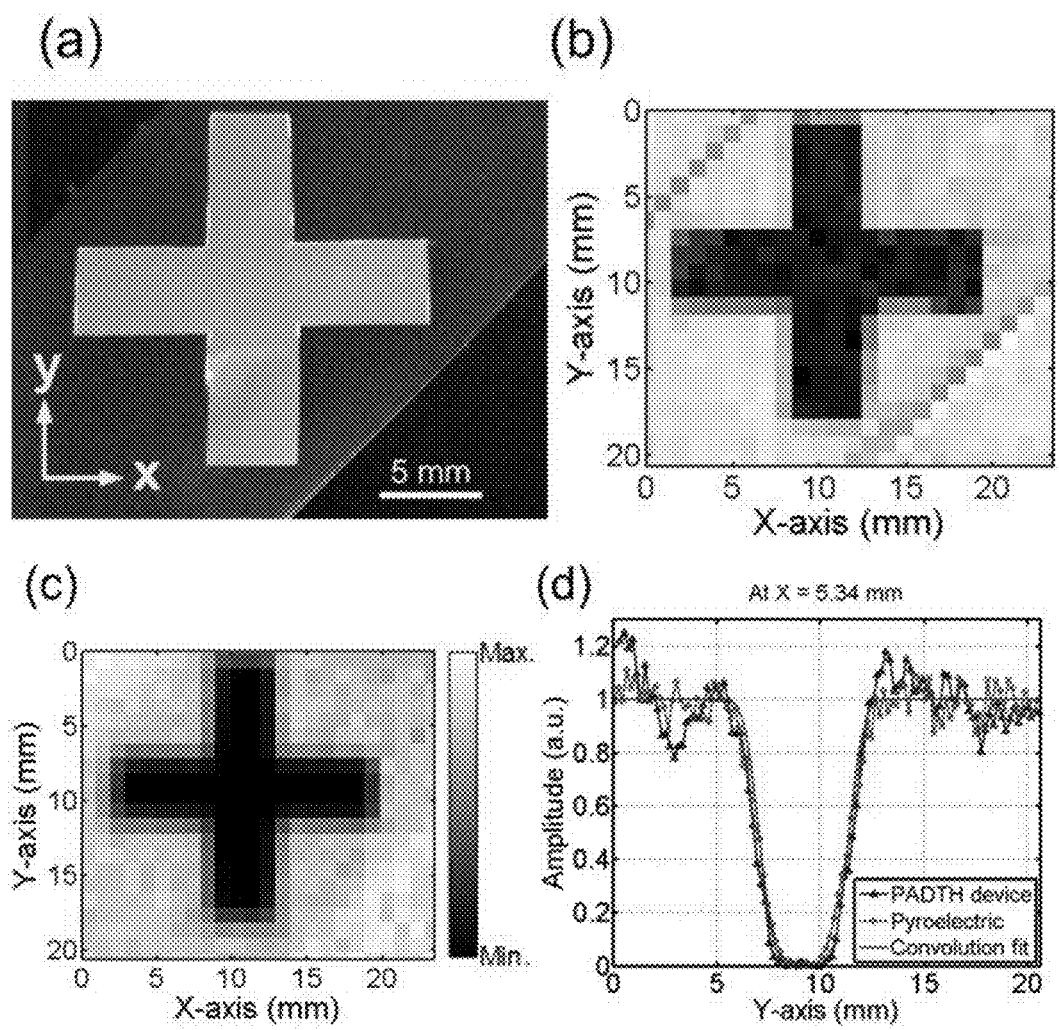

FIGS. 10(a)-10(d) demonstrate imaging by a photoacoustic terahertz detector device (PADTH) according to certain aspects of the present disclosure. FIG. 10(a) shows a photograph of a sample of aluminum foil. Scanned images with a scanning step size of 1 mm. FIG. 10(b) is an image taken with the PADTH detector. FIG. 10(c) is taken with a pyroelectric detector. FIG. 10(d) shows a one-dimensional (1-D) image with a scanning step size of 0.2 mm taken along y direction by the PADTH device and the pyroelectric detector. A comparison of the convolution fit is also plotted.

Figure 11:
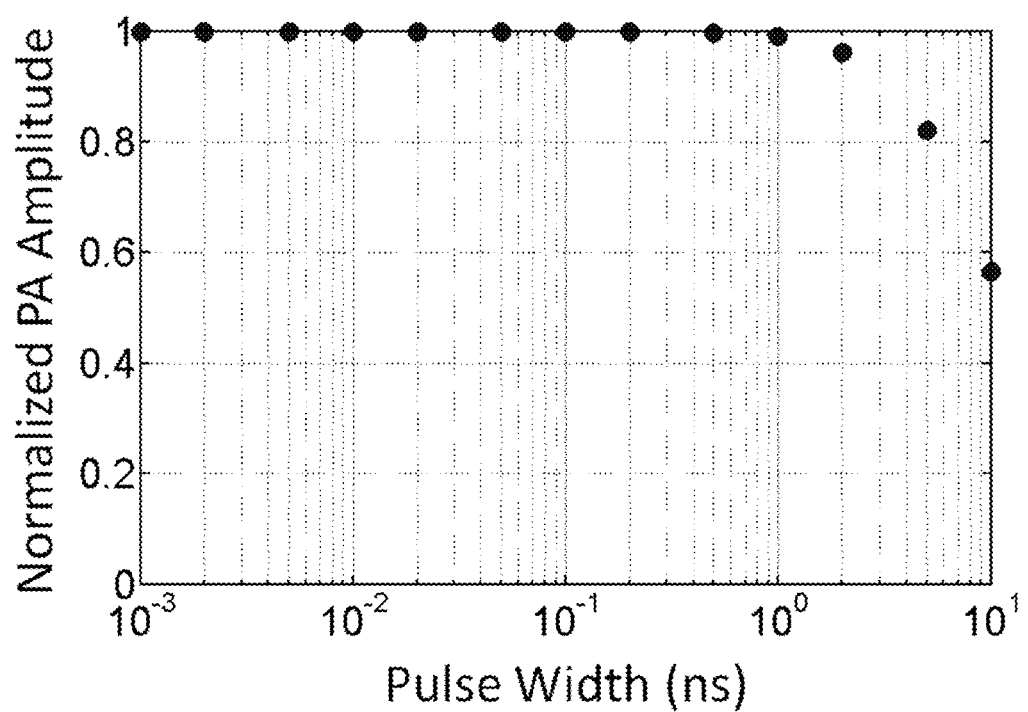

FIG. 11 shows response with respect to excitation pulse widths by a photoacoustic terahertz detector device (PADTH) according to certain aspects of the present disclosure. The calculated results of the response of normalized PA amplitude with various excitation pulse widths (1 ps to 1 ns) with fixed pulse energy with the assumption that no sample damage occurs.

Figures 12A, 12B, 12C:
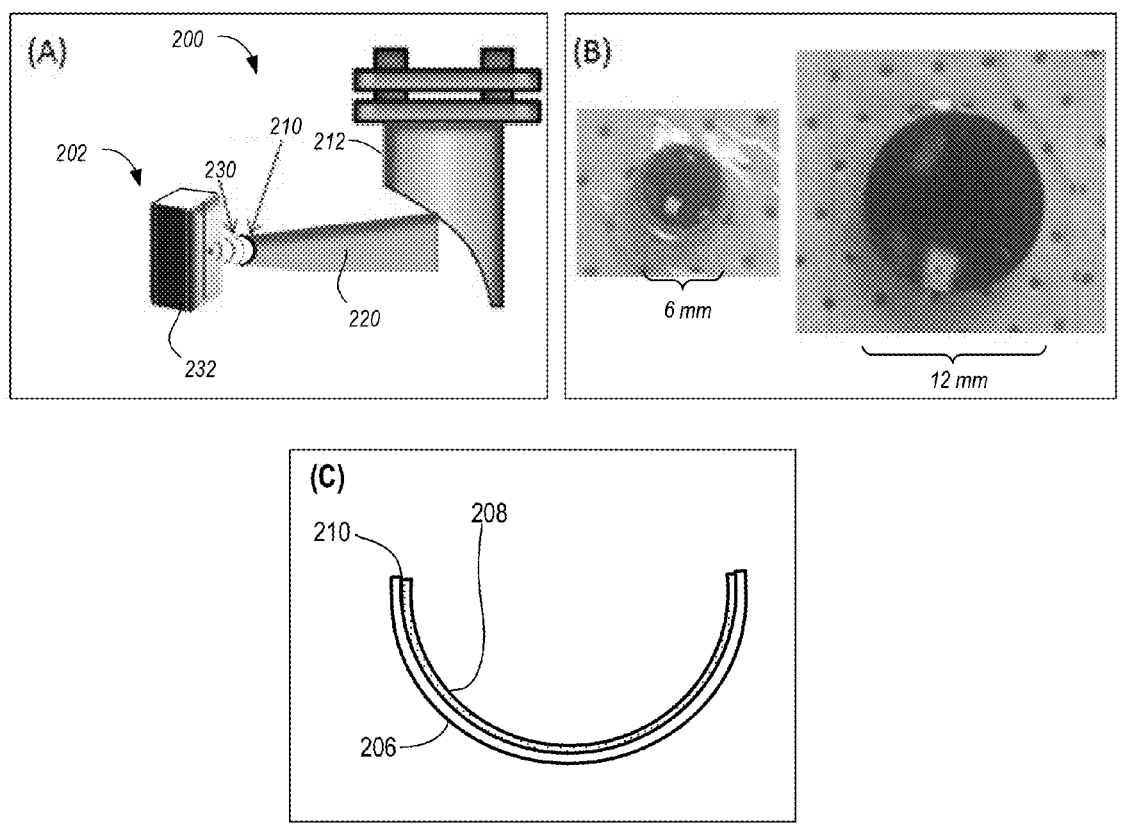

FIGS. 12(a)-12(c) show a THz detection device according to certain variations of the present disclosure. FIG. 12(a) is a schematic showing a PADTH with improved sensitivity provided by including an optoacoustic lens that further focuses acoustic pressure to an acoustic focal size on the order of tens of micrometers achieved by configuring the transducer material (composite) in the form of the optoacoustic lens. FIG. 12(b) shows photographs of two THz transducer optoacoustic lenses formed of a CNT-PDMS composite in accordance with certain aspects of the present disclosure. The lens on the left has a diameter of 6 mm and the lens on the right has a diameter of 12 mm. The lenses are used for laser-generated focused ultrasound. FIG. 12(c) is a schematic showing an optoacoustic lens having THz absorbing composite layer that may be formed by growing CNTs on the concave side of the plano-concave fused silica lenses followed by overcoating and infiltrating PDMS over the CNTs to form the composite layer.

Figures 13A, 13B:
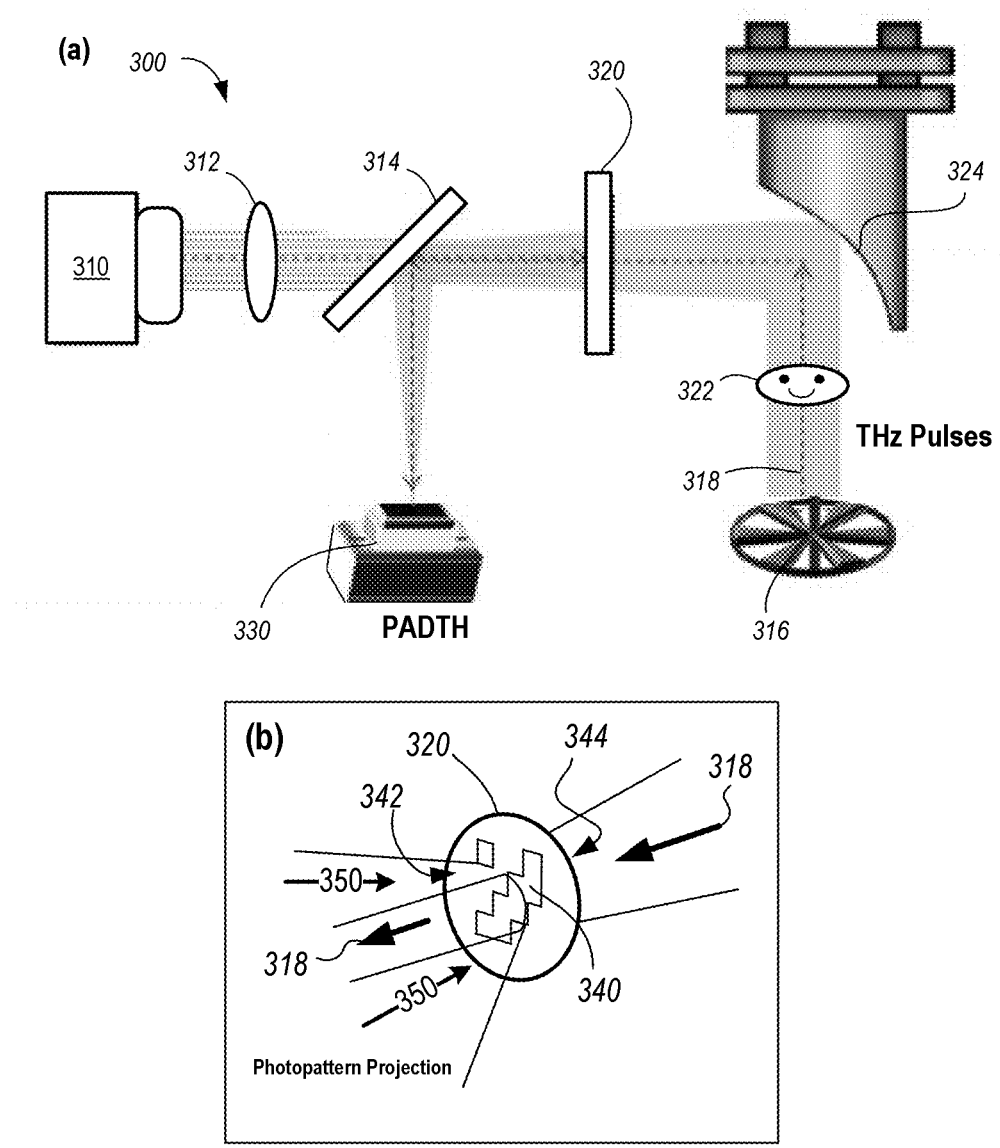

FIGS. 13(a)-13(b) show a THz detection system according to certain variations of the present disclosure. FIG. 13(a) is a schematic setup for a system for THz modulation and reconfigurable THz quasi-optical component using a photo-induced pattern on a semi-insulating silicon substrate that is illustrated in FIG. 13(b). The photoacoustic terahertz detector device (PADTH) according to certain aspects of the present disclosure in FIG. 13(a) is used to detect modulated THz pulse radiation.

Corresponding reference numerals indicate corresponding parts throughout the several views of the drawings.

DETAILED DESCRIPTION

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters.

In addition, disclosure of ranges includes disclosure of all values and further divided ranges within the entire range, including endpoints given for the ranges.

In various aspects, the present disclosure provides improved methods and systems for detection of radiation, such as terahertz (THz) radiation. By way of background, detection techniques and systems for THz radiation can be divided into two groups: coherent and incoherent detection (also called direct detection) systems. In accordance with the present disclosure, a new direct detection system is provided for broadband detection of signal amplitude. A number of direct detection technologies have been previously developed. Cooled detectors (that require cooling or cryogenic systems) such as hot-electron nanobolometers provide fast response time and high sensitivity, but their usefulness is limited due to the requirement of low operating temperature. Uncooled THz detectors, such as Golay cells and pyroelectric detectors, are commercially available, but have only modest sensitivity. Further, their response time is relatively long, about $10^{-2}$ to $10^{-3}$ seconds, hindering any capability for real-time THz detection due to the low-frequency modulation required for operation.

In particular, THz pulse radiation has been used extensively in a variety of areas from fundamental scientific research to practical applications. In physics and material science, examples include the study of carrier multiplication. Intense THz pulses can be used in nonlinear THz spectroscopy of semiconductors, THz nonlinear optics, vibrational excitation, and in activating DNA damage response in human skin tissue. THz pulsed spectroscopy and THz pulsed imaging are two novel techniques for the physical characterization of pharmaceutical drug materials. The characterization of THz pulse energy plays an important role in various applications. In conventional systems, thermal detectors are used that utilize continuous heat integration to measure the power, and then convert to energy according to pulse repetition frequency (PRF). Since most thermal detectors are slow in response, the characterization of the energy of each THz pulse at high PRF is restricted, especially for the applications with high fluctuation in pulse-to-pulse energy.

The temperature rise in a material due to the absorption of EM radiation can also produce other measurable physical effects. For example, a photoacoustic (PA) effect is the generation of high-frequency sound waves by absorption of a light pulse. In accordance with certain aspects of the present disclosure, THz radiation induces a PA effect by using a preselected THz absorbing material that serves as a photoacoustic transducer to generate ultrasonic waves through thermal expansion. Therefore, the ability to detect and listen to the generated acoustic wave is a new approach to THz pulse detection.

In various aspects, the present disclosure provides methods and systems for detection of radiation, such as terahertz (THz) radiation, by using devices capable of optoacoustic generation of acoustic (e.g., ultrasonic) energy that is detected by a sound detector component. An efficient transducer component is used to convert THz pulse energy to acoustic energy, such as ultrasound. The present disclosure thus provides a new technology for THz detection based on the photoacoustic (PA) effect, converting THz radiation into sound. Thus, the present disclosure contemplates detection of THz pulse radiation. A pulse includes discontinuous THz energy (e.g., bursts of THz energy). In other aspects, the present disclosure contemplates detection of modulated and pulsed THz radiation, where the pulses of radiation are further modulated. In yet other aspects, the present disclosure contemplates detection of polarized THz radiation and/or the ability to determine a polarization state of the THz signals received. Compared with conventional THz pulse detection systems, PADTH devices according to the present disclosure directly detect the energy of each individual THz pulse. Moreover, PADTH methods according to certain aspects of the present disclosure respond only to the pulse excitation, while rejecting other continuous radiation waves. Thus, when PADTH is employed for THz pulse detection, the ultimate sensitivity will not be restricted by the background continuous radiation, thus providing techniques for efficient detection of THz pulse energy.

The present disclosure thus provides new methods and devices for simultaneously providing room-temperature operation, fast response time, and good sensitivity. Furthermore, the devices of the present disclosure have small dimensions, enhancing the feasibility of developing miniaturized THz detectors and therefore providing an ability to expedite practical and commercial applications.

Figure 1:
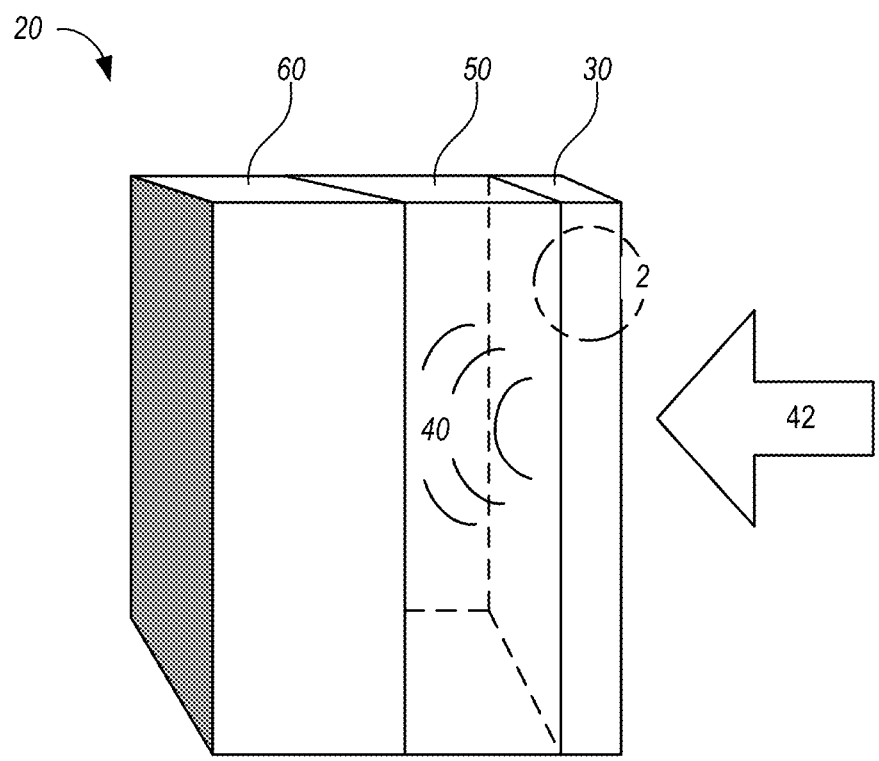
FIG. 1 is an exemplary schematic of a detection device according to certain variations of the present disclosure having a photoacoustic transducer and an acoustic sensor device.
Figure 2:
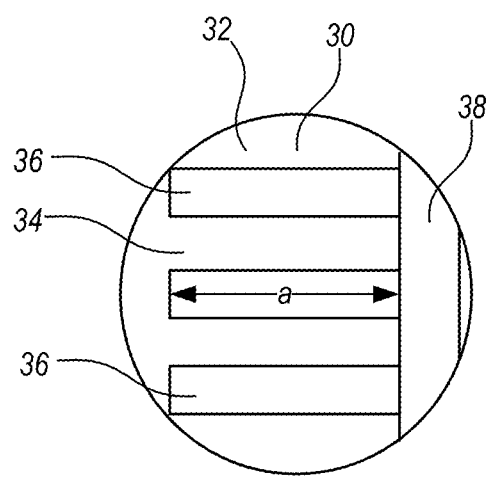
FIG. 2 is a sectional detailed view of the photoacoustic transducer component of FIG. 1 showing a composite material having a plurality of radiation absorbing particles and a dielectric matrix material.

In certain aspects, the present disclosure contemplates a system or device for detecting radiation that comprises a photoacoustic transducer configured to receive a pulse of terahertz (THz) radiation. An exemplary, simplified THz radiation detection device 20 is shown in FIG. 1. The device 20 has a photoacoustic transducer 30. As best shown in FIG. 2, in certain variations, the photoacoustic transducer 30 may be a composite material 32 that has a dielectric matrix material 34 and a plurality of radiation absorbing particles 36 distributed in the dielectric matrix material 34. The plurality of radiation absorbing particles 36 may be grown on a substrate 38, so that they have a major axis ("a") that intersects with the substrate 38. In certain variations, the composite material 32 may comprise carbon nanotubes (CNTs) as the radiation absorbing particles 36 and a polymer as the dielectric matrix material 34. The polymer or dielectric matrix material 34 can infiltrate within the CNT network, resulting in a CNT-polymer composite material 32. The individual CNTs are surrounded by the polymer that can be thermally expanded. In certain aspects, introduction of the dielectric matrix material 34 can cause the radiation absorbing particles 36 to be redistributed or reorganized from the original perpendicular "forest" orientation. In certain aspects, the radiation absorbing particles 36 are thus no longer well aligned, but have a more random orientation, which is advantageous for enhancing efficiency of THz absorption. The photoacoustic transducer 30 thus produces one or more acoustic waves 40 in response to receiving the pulse of THz radiation 42. In certain preferred variations, the generated acoustic waves 40 are ultrasonic waves, which generally have a frequency of greater than 20 kHz up to hundreds of MHz.

The device 20 further includes a coupling medium 50 and an acoustic detector or sensor 60 configured to receive the acoustic waves 40 produced by the photoacoustic transducer 30. The coupling medium 50 is optionally provided between the photoacoustic transducer 30 and the acoustic sensor 60 to enhance transmission of acoustic waves 40 therebetween (e.g., for sound coupling). The coupling medium 50 may be an ultrasonic gel or other material well known in the art for transmitting target acoustic waves. The converted acoustic (e.g., ultrasonic) waves 40 are thus transmitted to and detected by the acoustic sensor 60. The acoustic sensor may be a piezoelectric based acoustic detector. In certain aspects, the acoustic sensor 60 may be a highly sensitive acoustic sensor, e.g., an optical microring resonator, as will be described further below. Such THz radiation detection device 20 may be incorporated as a component into a larger device or system.

As will be described herein, the detector systems/devices and methods of the present disclosure have many advantages compared to existing and pyroelectric detectors, thus offering great potential for various THz applications. The terahertz sensing technology of the present disclosure utilizes the photoacoustic effect by converting terahertz radiation into sound. The sensing mechanism of the present technology thus overcomes the challenges observed with various conventional designs, such as bolometers or nanobolometers, Golay cells, and pyroelectric detectors. For example, devices prepared in accordance with various aspects of the present disclosure can operate at room temperature for easy and low-cost operation, have fast response times (e.g., on the order μs) allowing real-time detection, small dimensions or size and thus a small footprint, permitting easy integration into on-chip designs, and high sensitivity, by way of non-limiting example.

The present disclosure also provides new methods of photoacoustic detection of THz (PADTH) pulse radiation. The transient and localized heating that occurs in the photoacoustic transducer, for example, in a composite material comprising a carbon nanotube and polymer, by the absorption of THz pulse energy produces ultrasound, which is subsequently detected by a highly sensitive acoustic sensor. Different from the conventional thermal detectors utilizing continuous heat integration, this new method of THz detection responds to the energy of each individual THz pulse by a time-gated scheme, thus rejecting the continuous radiation from the ambient. In addition, the various embodiments of the present disclosure confer various advantages, including room-temperature operation, a fast response (e.g., on the order of about 0.1 microsecond (μs)) allowing real-time detection, compact size (e.g., mm scale), and wide spectral response, by way of non-limiting example.

The photoacoustic transducer comprises a THz absorbing material and is configured to receive a pulse of terahertz (THz) radiation and to produce one or more acoustic waves in response to receiving the pulse of THz radiation. The THz absorbing material may be in a liquid phase, a solid phase, a semi-solid phase, or combinations thereof (depending on environmental condition changes or if distinct layers of materials are used). The THz absorbing material may be a composite material having a dielectric matrix material, such as a polymeric material, and a plurality of radiation absorbing particles distributed in the dielectric matrix material. In other variations, the THz absorbing material optionally comprises a dielectric material like a doped semiconductor (e.g., Si) material. In yet other variations, the THz absorbing optoacoustic transducer component may be a metamaterial structure, for example, comprising one or more metallic structures and one or more dielectric materials. In certain other variations, THz absorbing material may be applied in discrete regions and thus define a pattern on a substrate. For example, where the THz absorbing materials are patterned into an array of stripes or rows, this provides anisotropic absorption characteristics of the THz radiation. An array may include a plurality of stripes or rows that may be parallel to one another or intersecting with one another. Such anisotropic structures can preferentially absorb THz radiation of a particular polarization, thus making the detection system capable of detecting polarized THz radiation or determining a polarization state of the THz signals received.

The optoacoustic transducer component thus optionally comprises a composite material having a dielectric matrix material, such as a polymeric material, and a plurality of radiation absorbing particles distributed in the dielectric matrix material. For example, the polymer may be an elastomer. It is desirable to maximize radiation pulse absorption to the composite material, while also maximizing thermal expansion, so that absorbed energy can be efficiently converted to volumetric expansion that results in physical displacement. In certain aspects, the polymeric material has a large coefficient of thermal expansion. The polymeric material may thus comprise an elastomer, such as a siloxane, like polydimethylsiloxane (PDMS).

In certain embodiments, a plurality of energy or radiation absorbing moieties or particles is preselected to be strongly absorptive for the wavelengths of electromagnetic radiation to be applied or detected, for example, terahertz electromagnetic waves (having a wavelength of greater than or equal to about 100 µm to less than or equal to about 1 mm with frequencies ranging from greater than or equal to about 0.1 THz to less than or equal to about 10 THz). In certain aspects, a strongly radiation absorbing material absorbs or has an extinction of greater than or equal to about 60% of the electromagnetic radiation that is applied to the material; optionally greater than or equal to about 70%; optionally greater than or equal to about 75%; optionally greater than or equal to about 80%; optionally greater than or equal to about 85%; optionally greater than or equal to about 90%; optionally greater than or equal to about 95%; and in certain variations, optionally greater than or equal to about 97% of the electromagnetic radiation that is applied to the material. In certain aspects, the radiation absorbing material absorbs greater than or equal to about 50% to less than or equal to about 100% of light directed at the material. In certain aspects, the plurality of light absorbing moieties is a solid or a liquid having the ability to absorb radiation, as discussed above.

In certain variations, the plurality of radiation absorbing particles comprises axially shaped particles, such as carbon nanotubes. In other alternative variations, depending upon the wavelength of radiation to be applied, the radiation absorbing particles may be selected from graphene oxide, gold particles (e.g., gold nanoparticles), silver particles, silver quantum dot particles, doped silicon, light absorbing metamaterial structures or other particles having strong broadband THz radiation absorbing properties, such as water (droplets), and any combinations thereof. It should be noted that in certain alternative variations, the material may be a radiation absorbing layer (which may or may not include a composite material) formed of a single species or material, e.g., a doped silicon material or a metamaterial structure (e.g., a stack of distinct dielectric and metallic layers) that serves to absorb radiation as desired. Such a radiation absorbing layer may be a solid or liquid.

In certain variations, the radiation absorbing particles are carbon nanotubes that comprise graphene, such as multi-walled carbon nanotubes or single-walled carbon nanotubes, oxidized forms of graphene, and any combinations thereof. In certain aspects, the radiation absorbing particles may comprise carbon nanotubes, graphene oxide, or combinations thereof. In particularly desirable variations, the plurality of radiation absorbing particles comprises multi-walled carbon nanotubes. Carbon nanotubes as radiation absorbing particles are particularly desirable, because such carbon nanotubes absorb incident radiation efficiently across a very wide spectral range (0.2-200 µm) and thus desirably provide for broadband THz detection.

Thus, in certain variations, the photoacoustic transducer comprises a carbon nanotube (CNT)-PDMS nanocomposite. The CNT-PDMS nanocomposite is used as a THz-to-ultrasound converter because CNTs can provide efficient conversion of absorbed THz radiation into thermal energy by their THz absorption capability (high optical absorption in the THZ range) and low specific heat. On the other hand, though CNTs are perfect broadband absorbers, they cannot provide sufficient thermal expansion required to generate strong acoustic waves for a transducer. The elastomeric polymer, polydimethylsiloxane (PDMS), has a high thermal coefficient of volume expansion that helps generate high amplitude pressure waves. Suitable PDMS polymer has a high thermal coefficient of volume expansion (e.g., 960× $10^{-6}$ $K^{-1}$) which is 3-4 fold higher than those of water and typical polymers, and about 20 fold higher than those of typical metals. The PDMS thus interfaces with CNT radiation absorbers within the composite material to function as an effective acoustic transducer.

In certain aspects, the nano scale nature of the CNTs also facilitates efficient heat transfer to the surrounding PDMS on the order of nanoseconds. Therefore, both the radiation absorbing particles and the dielectric polymeric material contribute to efficient PA conversion of THz radiation. Another consideration for the design of the THz-to-PA transducer is the thickness of the composite material, because a thin composite film is preferred to avoid excess acoustic attenuation. However, the THz absorption coefficient of PDMS alone is only about 10 $cm^{-1}$, and the absorption by a 30 µm-thick PDMS film is only about 5% at 0.5 THz radiation. Therefore, including the radiation absorbing particles, like CNTs, within the composite is helpful to efficiently absorb THz radiation.

In certain aspects, a thickness of the composite material is less than or equal to about 50 µm. In certain variations, the thickness of the composite material is greater than or equal to about 25 µm to less than or equal to about 50 µm, optionally greater than or equal to about 30 µm to less than or equal to about 50 µm, and optionally greater than or equal to about 40 µm to less than or equal to about 50 µm, in certain variations. For example, a thickness of a composite material comprising PDMS and CNT nanoparticles may desirably less than or equal to about 50 µm. However, to maximize the THz absorption, a thickness of the as-grown CNTs is desirably not too thin. Thus, in certain aspects, the thickness of as-grown CNTs can be at greater than or equal to about 40 µm to less than or equal to about 50 µm. As for the final thickness of the CNT-PDMS composite (including both the CNTs and the PDMS), generally a thinner material layer is desired, because a thicker sample may result in unwanted acoustic attenuation in the composite. The counterexample of a thick sample of approximately 500 µm is shown in FIG. 3(a), where the unnecessary blank PDMS layer is disposed over the composite, which introduces excess acoustic attenuation. In certain aspects, a composite material having a thickness of at least about 30 µm is advantageous, because such thin free-standing films can still be handled without difficulty.

In alternative aspects, the composite material may be formed on or made into the shape of an acoustic lens, such that generated acoustic wave is focused to the acoustic sensor.

In certain aspects, the present disclosure further contemplates methods for detecting electromagnetic (EM) radiation, such as terahertz (THz) radiation. In certain aspects, the method for detecting terahertz radiation comprises generating an acoustic wave within a photoacoustic transducer by receiving a pulse of terahertz (THz) radiation. The photoacoustic transducer comprises a composite material having a polymeric matrix material and a plurality of radiation absorbing particles distributed in the polymeric matrix material. The method also includes detecting the acoustic wave with an acoustic sensor. In certain aspects, the generating and the detecting occur in less than or equal to about 1 ms, optionally less than or equal to about 500 µs, optionally less than or equal to about 100 µs, optionally less than or equal to about 50 µs, optionally less than or equal to about 25 µs, optionally less than or equal to about 10 µs, optionally less than or equal to about 1 µs, optionally less than or equal to about 0.5 µs, optionally less than or equal to about 0.1 µs, and in certain aspects, optionally less than or equal to about 0.01 µs.

In certain aspects, the detecting occurs real-time, meaning that in certain preferred aspects, the pulsed THz radiation is capable of being received and detected by the device having the photoacoustic transducer and acoustic sensor in less than any of the time frames specified above, especially less than 0.01 µs. The acoustic wave generated via the photoacoustic transducer is ultrasonic and may have a frequency of greater than or equal to about 20 kHz. In certain aspects, the acoustic wave is an ultrasonic wave having a frequency of greater than or equal to about 10 MHz and an output pressure of greater than or equal to about 10 Pa.

Thus, a photoacoustic (PA) wave is generated by the composite material due to the absorption of EM energy or radiation in the form of pulsed light. Briefly, a portion of the absorbed EM energy is converted into heat. Then, a temperature rise causes thermal expansion through the thermal-elastic effect, producing a pressure or acoustic wave that propagates away from the excitation region and can then be detected by downstream acoustic sensors, such as ultrasonic sensors. The generated PA pressure wave is thus collected and/or detected by the acoustic sensors. In certain aspects, the generated pressure wave is most efficiently collected when the frequency response of ultrasonic detectors matches the frequency spectrum of the generated PA signals. Thus, a sensitive ultrasonic sensor with proper bandwidth can be important.

The amplitude of the initial pressure $p_0$ upon illumination by a short EM pulse is governed by:

$$p_0 = \Gamma \eta_{th} \mu_\alpha F \quad (1),$$

where $\Gamma = (\beta v_s^2)/C_p$ is defined as the Grueneisen coefficient, $\beta$ is the thermal coefficient of volume expansion, $v_s$ is the speed of sound, $C_p$ is the specific heat capacity, $\mu_\alpha$ is the optical absorption coefficient, and F is the optical fluence, i.e., the optical energy per unit area. The factor $\eta_{th}$ is the percentage of absorbed energy that is converted into heat and can be assumed to be 1 in most cases. From the expression, $\Gamma$ is determined by the mechanical and thermal properties of the absorber (e.g., composite material) and is independent of the incident EM spectrum, while $\mu_\alpha$ is usually spectrally dependent. The initial pressure $p_0$ is proportional to the incident EM pulse energy; hence, if a THz pulse is incident on a material that can absorb the full bandwidth of the THz spectrum, the THz pulse energy may be detected directly via the generated acoustic wave. To enable broadband detection over the entire THz range, the sample with high absorption over the spectral bands of interest is desired.

As shown in equation (1), the Grueneisen coefficient determines the efficiency of PA conversion of the nanocomposite, including $\beta$ (the thermal coefficient of volume expansion), $v_s$ (the speed of sound), and $C_p$ (the specific heat capacity). The advantage of using PDMS as surrounding media, rather than water surroundings, of the CNT radiation absorbing particles for PA generation mainly relies on the improved thermal expansion coefficient and lower specific heat capacity while the effect of the speed of sound should also be taken into account. Table 1 shows a comparison of the thermal and acoustic properties of PDMS and water. Compared with water surroundings, the improvement of PA conversion benefited by PDMS is about 6 times.

TABLE 1

Thermal and acoustic properties of PDMS and water

| Material | Thermal expansion coefficient ($10^{-6}$/K) | Speed of sound (m/s) | Specific heat capacity (J/g · K) |
|---|---|---|---|
| Water | 207 | 1480 | 4.19 |
| PDMS | 960 | approximately 1000 | 1.46 |

In certain aspects, the dielectric material of the composite material is a polymeric material comprising polydimethyl siloxane. In certain preferred aspects, such a polymeric material is a high modulus material. By high modulus material, it is meant that the Young's modulus of the material is greater than or equal to about 0.1 MPa, and optionally greater than or equal to about 1 MPa. High modulus PDMS, allows for a thinner elastomer coating than many conventional PDMS materials made from the commercial Sylgard-184 precursors and it has a higher cross-linking density that improves the modulus of the material as well. One particularly suitable high modulus PDMS material has a Young's modulus of about 11 to about 12 MPa. One particularly suitable high modulus PDMS has four components, a vinyl-terminated PDMS, a methylhydrosiloxane copolymer, which acts as a crosslinker, a platinum (Pt) catalyst, and an inhibitor. The inhibitor is an unsaturated organic ester that coordinates to the Pt catalyst and keeps it inactive at ambient temperature. Above about 80° C., the inhibitor is broken and the Pt catalyst is then activated. Small quantities of both (e.g., less than 1 wt. %) is sufficient for the polymerization.

In certain aspects, the PDMS can be prepared by mixing a base (vinyl terminated PDMS, DMS-V03, M.W.: 500-600, commercially available from Gelest), cross linker (7048 cross linker) and inhibitor (1371 inhibitor), and Pt catalyst (4000 Pt catalyst) all from Dow Corning. First, the base is mixed with Pt catalyst with a weight ratio of 10 g:0.2685 g in one vial, and cross linker is mixed with inhibitor with a weight ratio of 2.0538 g:0.03 g in another vial. Then, the two vials are mixed and shaken by hand or stirrer. The modulus of this cross linked PDMS is typically about 11 to about 12 MPa.

To make the composite for PADTH, multi-walled CNTs (MWCNTs) are first grown on an oxidized silicon substrate catalyzed with 1 nm-thick Fe film by a chemical vapor deposition process. In certain variations, an average diameter of the grown MWCNTs may be greater than or equal to about 5 nm to less than or equal to about 25 nm. An average height of each carbon nanotube may be greater than or equal to about 1 micron to less than or equal to about 500 micron and spacing between adjacent carbon nanotubes is greater than or equal to about 25 nm to less than or equal to about 250 nm, optionally greater than or equal to about 75 nm to less than or equal to about 125 nm, in certain variations.

Thus, an average diameter of the grown MWCNTs in the forest may be about 10 nm and interspacing may be about 100 nm for certain embodiments. The CNT forest morphology is controlled to enable sufficient interspacing (100 nm) among the CNTs to facilitate infiltration by the PDMS when it is introduced (e.g., poured onto) the CNT forest. The ability to disperse the polymeric material among the radiation absorbing particles ensures efficient PA conversion throughout the three-dimensional composite matrix. The as-grown CNT forest is controlled to be 40-50 μm in height (FIG. 3(a)) to facilitate the PDMS infiltration. Otherwise, the PDMS can hardly infiltrate the plurality of CNTs to form a uniform composite structure. Generally, these difficulties occur where the as-grown CNTs are too thick (e.g., greater than about 50 μm).

After PDMS infiltration, the CNT-PDMS composite is pressed with a fluorosilane-treated slide glass with a 25 μm-thick spacer inserted between the substrate and the slide glass to roughly control the film thickness. The composite is then thermally cured at 100° C. for 10 minutes to have the final thickness of about 30 μm throughout the film, where the CNTs are uniformly embedded in PDMS, as shown in FIG. 3(b). Considering the as-grown CNTs' packing fraction is around 1.6%, the final CNT fraction within the composite is approximately 2.7% [=1.6%×50/30]. Finally, the film is carefully peeled off from the substrate, so that a thin free-standing composite film is obtained.

The removal of the substrate is necessary to avoid either THz reflection/absorption or ultrasound attenuation by the substrate. That is, the thin elastomer film with embedded CNTs facilitates both high THz absorption and low acoustic attenuation. The fabrication process is also easily scalable to large areas or multiple samples for practical applications. A scanning electron microscope image presenting a cross-sectional view of CNT-PDMS composites with different thickness of spacers is shown in FIGS. 3(a)-3(b).

The composites are made with a thick spacer of 0.5 mm FIG. 3(a) and a thin spacer of 25 μm FIG. 3(b). In FIG. 3(a), the pure PDMS layer is too thick and thus is less suitable as a PA transmitter. The inset in FIG. 3(a) shows the CNT forest with a length of about 45 μm before PDMS infiltration. Compared with the visible nano scale texture of CNTs in FIG. 3(a), most CNTs are invisible in FIG. 3(b), because more PDMS encompasses the boundaries due to more pressing.

To detect the acoustic waves generated by the absorption of THz pulses by the composite materials (e.g., the CNT-PDMS composite film), the acoustic sensor may be a photonic sensor, such as a polymeric microring resonator, as a highly sensitive ultrasonic detector having wideband acoustic response. The design and working principles of the microring resonator as an ultrasonic sensor has been described in Ling, et al., "High-sensitivity and wide-directivity ultrasound detection using high Q polymer micro-ring resonators," *App. Phys. Lett.* 98, 204103 (2011); Maxwell, et al., "Polymer microring resonators for high-frequency ultrasound detection and imaging," *IEEE J. Sel. Top. Quantum. Electron.* 14, 191-197 (2008); Chao, et al., "High-frequency ultrasound sensors using polymer microring resonators," *IEEE Trans. Ultrason. Ferroelect. Freq. Contr.* 54, 957-965 (2007); and Hsieh, et al., "All-optical scanhead for ultrasound and photoacoustic dual-modality imaging," *Opt. Express* 20, 1588-1596 (2012), each of which is expressly incorporated herein by reference in its entirety. Briefly, the acoustic pressure modulates the optical resonance condition in the microring waveguide, leading to a shift of the resonance wavelength. When the microring is probed at a fixed wavelength tuned to a high slope region of the transmission spectrum, the ultrasound wave incident onto the microring translates into a modulation of the output optical intensity, which is then recorded by a high-speed photodetector. Therefore, a high quality (Q) factor of the optical resonance enables high-sensitivity detection.

In certain variations, the PADTH detector may be formed by placing the composite material (e.g., CNT-PDMS composite), as a THz-to-PA transducer, directly on the microring ultrasonic sensor. A coupling medium may be disposed between the photoacoustic transducer and the acoustic sensor to enhance ultrasound coupling. In certain variations, the coupling medium is a gel disposed between the composite transducer and the microring resonator. The diameter of the microring resonator may be 60 μm. Its wideband acoustic response (DC to approximately 100 MHz at −6 dB) enables efficient collection of PA signals excited by short THz pulses. Additionally, it can be made to 3 mm size or smaller, which is attractive for applications requiring compact THz detectors. The size of active element of the microring ultrasonic detector may be about 60 μm. With better dicing and fiber-coupling techniques (e.g., using a fiber circulator to access the input and output ports of the microring resonator), device sizes of sub-millimeter can be made. Another advantage is that arrayed microring detectors can be constructed with element spacing of ≤100 μm, where each microring sensor can be addressed by a single bus waveguide by using wavelength division multiplexing scheme. A feedback control can also be used on the optical output power of the microring device to ensure the stability of high-sensitivity operation.

Example 1

An exemplary complete system 100 for PA detection of THz pulses in this experiment is shown in FIG. 4. First, a source of radiation 110 is used THz pulse is provided. Briefly, a 500 Hz Ti-sapphire laser system (Lambda cubed system at University of Michigan) producing pulses with a wavelength of 800 nm, pulse energy of 3 mJ and pulse duration of 30 fs is used. A laser beam generated by the source of radiation 110 is then focused by a lens 112 to create plasma 114 at the focus. A BBO crystal 120 is positioned between the lens 112 and the focus to generate second harmonic at a wavelength of 400 nm; combining the fundamental and second-harmonic pulses coherently in air creates broadband radiation at the focus. Such a two-color air ionization scheme is able to generate broadband pulses extending from the THz€ to the mid-infrared regime.

The generated THz and MIR radiation 122 is collected and collimated by a parabolic metal mirror 130. A silicon wafer 132 is used to block the unwanted light at NIR and visible frequencies. To further block MIR component in the pulses, a commercial low-pass filter 134 (LPF 10.9, Tydex, Petersburg, Russia), which has a cut-off frequency at 6 THz (the frequency at which the transmission is 50% of the maximum value) and negligible transmission above 11 THz frequency is used. The produced spectra of the THz source used in the photoacoustic experiment are measured by Michelson interferometer, as shown in FIG. 7.

Second, the THz pulse radiation is focused onto an assembly forming a PADTH detector device 150 via a second parabolic metal mirror 140 with f=5 cm to a spot size of about 0.8 mm. The PADTH detector device 150 is mounted on a three-dimensional translation stage (not shown) and aligned at the focus of the parabolic mirror 140. The THz energy 152 is converted into pressure waves 154 via the PA effect (see inset) through a nanocomposite 160. The nanocomposite 160 comprises a CNT-PDMS composite.

To ensure the optimal fabrication of 3D CNT-PDMS composite, the thickness of as-grown CNTs is less than or equal to about 50 μm. Meanwhile, to maximize the THz absorption, the thickness of as-grown CNTs is also not too thin. Thus, in certain variations, a thickness of as-grown CNTs is prepared at about 40 to about 50 μm. As for the final thickness of the CNT-PDMS composite, thinner is generally more desirably, because a sample that is too thick may result in unwanted acoustic attenuation within the composite material. The counterexample of a thick sample of about 500 μm is shown in FIG. 3(a), where unnecessary blank PDMS layer left over the composite will introduce excess acoustic attenuation. An approximately 30 μm-thick composite is used, because such thin free-standing film can still be handled without difficulty.

As shown in FIG. 6, a characteristic transmission spectrum of the CNT-PDMS composite (thickness: approximately 30 μm) is obtained at frequencies of 0.2-3 THz using THz time-domain spectroscopy. The THz radiation is generated from a photoconductive emitter and detected by electro-optical sampling. The spectrum is calculated by performing Fourier transform to the time-domain waveform.

From the transmission spectrum, the CNT-PDMS composite is a fairly good absorber for frequencies above 1 THz. For frequencies smaller than 1 THz, the film thickness is too thin to absorb the radiation efficiently. The experimental setup of THz time-domain spectroscopy only allows measurement of the transmission spectrum. The CNT-PDMS composite may have some reflection, but it is believed that reflection is a minor effect, because the composite is very transparent at low frequencies, and optical properties of CNT and PDMS are not very dispersive in this spectral range. Thus, a conservative estimation of the absorption of the CNT-PDMS absorber (29 μm) is more than half at frequencies greater than 1 THz, which also suggests that the as-grown CNT with thickness of about 50 μm is sufficiently thick to collect THz energy.

An ultrasonic gel 156 in disposed between the nanocomposite 160 and an acoustic detector 162 for sound coupling. The PA pressure wave 154 is detected by the acoustic detector 162, which is in the form of an optical microring resonator, serving as a sensitive ultrasonic detector, and the modulated optical signal is subsequently amplified by a high-speed photodetector module 164 (New Focus, 1801-FC) has a dc output (3-dB bandwidth: DC-50 kHz) and an ac output (3-dB bandwidth: 25 kHz-125 MHz), which is finally recorded by a digital oscilloscope 166 (WaveSurfer 452, LeCroy, Chestnut Ridge, N.Y.) with a sampling rate of 1 GHz. The high-speed photodetector dc output can be used to monitor the microring's output at DC-50 kHz, and the ac output is mainly for high-frequency ultrasound recording. First, a transmission spectrum of the microring is measured before the THz experiment, where a high-sensitivity operating point can be determined, e.g., the optimal dc output value of the microring corresponding to the highest slope of the resonance. By monitoring the dc output, the probing wavelength can be controlled accordingly to maintain the output power of microring close to its optimal dc output value. Using this approach, thermal fluctuations that may cause the resonance shift of the microring resonator can be effectively balanced. Thus, the fluctuations in the sensitivity of the PADTH detector caused by thermal fluctuations are believed to be negligible.

Unlike PZT transducers, the sensitivity of microring detectors is not limited by their sizes (typically 50-100 μm in diameter). The generated acoustic signal amplitude is proportional to excited light energy density (fluence). Due to the characteristic of long wavelength at THz frequencies, the smallest focal spot size is relatively large, approximately 1 mm, resulting in much lower fluence compared with the spot size of micrometer scale achieved at visible wavelength. One way to improve the PADTH's efficiency is to further focus the acoustic pressure to an acoustic focal size of tens of micrometers by configuring the composite in the form of an optoacoustic lens, as illustrated in FIG. 8(A). That is, the optoacoustic lens can fully utilize the advantage of the small element size and high sensitivity of the microring detector for efficient PADTH detection. Thus, a CNT-PDMS optoacoustic lens can be used to focus the green-laser-excited pressure wave to a tight focal spot.

Thus, in order to maximize the PADTH efficiency, the probe laser wavelength is set to the highest slope of the microring optical transmission resonance (FIG. 5(a)). Thus, FIG. 5(a) shows an optical transmission spectrum of the polymer microring resonator, where the resonance bandwidth is approximately 60 μm. FIG. 5(b) shows the measured THz power by a pyroelectric detector at a modulation frequency of 5 Hz. The polymer microring has an optical Q factor of $1.3 \times 10^5$, translating into a pressure sensitivity of approximately 22 mV/kPa. The THz pulse energy measured using the PADTH is calibrated against a commercial pyroelectric detector (THZ5I-MT-BNC, Gentec-EO, Quebec, QC, Canada). To do so, the THz source is modulated at 5 Hz by a mechanical chopper, at which rate the best sensitivity of 70 kV/W of the pyroelectric detector is achieved. The mechanical chopper is placed before the focusing lens of the NIR laser. FIG. 5(b) shows the measured THz average power of 1.8 μW by the pyroelectric detector. Considering a PRF of 500 Hz, the THz energy and fluence per pulse are 3.6 nJ and approximately 0.72 μJ/cm² $[=(3.6 \text{ nJ})/(\pi(0.08/2)^2 \text{ cm}^2)]$, respectively.

FIG. 5(c) shows a single-shot PA waveform excited by one THz pulse with energy of 3.6 nJ (the signal-to-noise ratio (SNR) is 16.9 dB), while the inset shows a spectrum of THz pulse-excited PA waveform. At this THz energy, FIG. 5(c) shows the PA signal acquired by the PADTH detector. The measured peak voltage is approximately 15 mV, corresponding to a sensitivity of 4.2 mV/nJ of THz detection, and a pressure level of 680 Pa. Note that this pressure level is much lower than the ambient pressure of $10^5$ Pa. The inset in FIG. 5(c) shows the PA signal spectrum and FIG. 5(d) shows the enhanced signal-to-noise ratio (SNR) (the improved SNR is 21.5 dB) after applying a matched filter of 1-26 MHz. At this frequency range, the noise arising from ambient sound can be neglected due to their low frequency characteristics. Here, the primary interest is in the sound signal at frequencies of several to tens of MHz. At this frequency range, the sound attenuation coefficient in air (1.64 dB/MHz·cm) is significantly higher than that in water ($2.2 \times 10^{-3}$ dB/MHz·cm). Thus, the noise arising from ambient sound can be neglected due to extremely high attenuation of ultrasound in air, where the PADTH device is used in these examples.

The noise level of the detected PA signal is 0.92 mV after applying the matched filter, corresponding to a noise-equivalent detectable energy (NEDE) of THz pulses of approximately 220 pJ. The time-domain PA signal is excited by one THz pulse without signal averaging, which also demonstrates the feasibility of real-time detection of THz pulses. The distance between the CNT-PDMS composite and the microring are determined to be 0.9 mm using the known sound speed of gel (approximately 1500 m/s). The detector response time is essentially determined by the time required to generate a PA signal and the detected acoustic pulse duration (or bandwidth). The latter means a complete PA waveform should be received to have sufficient information (usually the peak value) to determine the THz energy. In this case, the latter dominates, achieving the response time less than 0.1 µs. The less than 0.1 µs time scale is several orders faster than conventional pyroelectric detectors (0.1 s). The detected acoustic bandwidth appears to be somewhat limited by the sample thickness. The response time can therefore be further enhanced by employing a thinner composite material to generate shorter acoustic pulses. It is worth noting that lower THz energies can be detected using the PADTH by signal averaging, but with a trade-off in measurement time.

Example 2

The ability of real-time detection of a PADTH device in accordance with certain aspects of the present disclosure is validated in a second experiment. A mechanical chopper placed before the focusing lens of the NIR laser is used to implement a gated THz pulse train. The chopper is set at different frequencies to control the number of pulses passing through for PA excitation, and the time elapsed between two adjacent trains of pulses. The laser beam before focusing had a diameter of 5 mm on the chopper with a gap of approximately 10 mm between each flabellum. A schematic is shown in FIG. 8(a). The chopper frequencies are set at 63, 125, and 250 Hz, respectively.

FIG. 8(b) shows the recorded PA signals as a function of elapsed time at the chopper frequency of 63 Hz. FIG. 8(c) shows the peak amplitude of the PA signal after Hilbert transform (envelope) as a function of each THz pulse. Results of 3 different designated frequencies of the chopper are plotted, where the PADTH detected pattern agrees well with the set frequencies of the chopper. The complete "on" and "off" of PA excitation in the cases of 125 and 250 Hz is evident, while there is some intermediate amplitude value detected in the case of 63 Hz. This is because the comparable sizes of the laser beam spot and the gap between each flabellum of the chopper, resulting in the partial blocking of NIR laser and thus, the intermediate THz energy.

It is important to examine the linear response of a PADTH device between the incident pulse energy and the output signal. Therefore, measurements are performed with different energy settings of the THz source. The pulse energy is calibrated by a bolometer (HD-3, Infrared Laboratories, Inc., Tucson, Ariz.), which can detect EM radiation below 15 THz, covering the spectral range of the THz source used here. Since the THz polarization is close to linear, a THz polarizer (G30×10-S, Microtech Instruments Inc., Eugene, Oreg.) is used to achieve different THz energy by rotating the polarizer at different angles. Several values of THz pulse energy are calibrated with the bolometer, and they are used for calibrating the PADTH response. Measurements of PA signals by PADTH are performed for 80 times for each case to average over the energy fluctuations of the THz source. FIG. 9 shows the resultant PA signal acquired by the PADTH detector as a function of the energy of the THz radiation, confirming a linear dependence. Although the bolometer suffers lower sensitivity for strong EM radiation, i.e., a nonlinear response, the range of THz pulse energy used in this calibration is less than 3-fold, and thus, it is believed that the bolometer would still function linearly.

Example 3

The usefulness of the PADTH detector according to certain aspects of the present disclosure is demonstrated by showing its applicability to imaging in this example. A photograph of the sample to be imaged, an aluminum foil having a cross pattern attached on optically transparent tape, is shown in FIG. 10(a). The sample is mounted on an x-y stage and scanned through the position slightly beyond focus while the PADTH detector is aligned at the focus. FIGS. 10(b) and 10(c) show the acquired images of the aluminum foil sample radiated by the THz source. FIG. 10(b) shows the measurement with the PADTH detection, whereas FIG. 10(c) is a reference image taken with the commercial pyroelectric detector, the same one used to obtain FIG. 10(b) (THZ5I-MT-BNC, Gentec-EO, responsivity=70 kV/W, NEP=1 nW/Hz$^{1/2}$). Both methods are able to clearly image the aluminum pattern.

One interesting and unexpected finding is that the PADTH device can clearly image the boundary between the tape and the air, while the pyroelectric detection did not. This is believed to be because THz beam scatters on the boundary, resulting in lower energy density (fluence) that can be detected and distinguished by the PADTH, demonstrating the unique detection mechanism of the PADTH platform. In contrast, the pyroelectric detector measured the power inside its aperture of 5 mm, which is large enough to collect most power although slight scattering occurred. The resolution for both images is determined by the scanning step size, which is 1 mm in each direction.

FIG. 10(d) shows the THz image in one dimension (1-D) acquired by the PADTH and the pyroelectric detector with a scanning step size of 0.2 mm along the y direction. From FIG. 10(d), it can be clearly seen that the 1-D profile by the two methods are in good agreement. For quantitative analysis, a convolution of a THz Gaussian beam and a THz transmission function are shown, produced by the aluminum sample, to fit the 1-D image. The THz transmission function (i.e., the sample width) along y direction at x=5.34 mm is 4.4 mm. By applying convolution fits, it is determined the THz beam size is 2.2 mm in y direction. The larger beam size than THz focal spot size of 0.8 mm is reasonable considering the Al sample is placed beyond the THz focus. Compared with the pyroelectric detector, the PADTH detector has potential for real-time THz imaging.

In the initial THz imaging experiment, the components in the THz imaging system are not optimized to fully utilize the fast detection of the PADTH detector. The speed of the exemplary tested current system appears to be limited by the data acquisition and sample translation facilities, taking the acquisition time of 2 seconds for one pixel. Thus, the total measurement time required for the PADTH device and the pyroelectric detectors does not make much difference. Nowadays high-speed PA (or other modality) imaging system employ a PC digitizing card with an on-board segmented memory architecture and fast scanning mirror. If such components are integrated into the THz imaging experiment, the imaging speed will be mainly restricted by the repetition rate of the light source by PADTH. Considering a THz source with PRF of 500 Hz, the measurement time for an image consisting of 25×25 pixels by PADTH and by the pyroelectric detector (0.2 sec for 1 pixel due to 5 Hz modulation) will be 1.25 s [=25×25/500] and 125 s [=25× 25×0.2], respectively, showing 100 times faster imaging time by using PADTH. Certainly, this is not the limit of PADTH device in this case, because the speed can be further improved if higher PRF of THz source is available. In contrast, increasing PRF of THz source will not improve the imaging speed of the pyroelectric detector anymore.

It is noted that the PADTH technique in accordance with certain aspects of the present disclosure is different from other techniques using PA effects in a PA cell for THz detection, such as Golay cells and tuning fork-based THz detection. Both of the two examples utilize PA effects (e.g., heat-induced expansion effects) at thermal equilibrium of the whole PA cell, which may result in slow response time. In the PA cell, the sensitivity is usually independent of the optical fluence once the irradiated spot size is smaller than the sensing area. In contrast to the conventional PA cells, the techniques in accordance with certain aspects of the present teachings are based on the detection of high-frequency acoustic waves launched by the absorption of pulsed radiation by means of transient and localized heating and expansion in an absorber. The transient heating benefits fast detection of PADTH. Besides, the localized heating generates thermoelastic waves whose pressure level is proportional to the optical fluence. Therefore, the pressure level, and thus the sensitivity of PADTH device, may be much enhanced by tightly focusing the THz radiation.

Another conventional work utilizing THz-enhanced acoustics (TEA) employs different mechanisms from PADTH for THz detection. For example, a TEA method is described in Clough, B., Liu, J., and Zhang, X.-C., "Laser-induced photoacoustics influenced by single-cycle terahertz radiation," *Opt. Lett.*, 35, 3544-3546 (2010), the relevant portions of which are incorporated herein by reference. This TEA method has to generate laser-induced plasma by focusing intense femtosecond laser pulse before THz detection, which involves more complex facilities compared with the inventive PADTH detection method. The detected PA signal by the PADTH method essentially "gates" the THz pulse excitation, thus rejecting continuous radiation, such as blackbody radiation. When used in THz pulse detection, the detection limit of the PADTH devices is not limited by such "background" radiation. Such characteristics of rejecting continuous radiation will be advantageous, including when other noises associated with the inventive PADTH detection system can be further reduced and the continuous radiation begins to dominate.

To understand the ability to "gate" the THz pulse excitation by the inventive PADTH techniques, dependence of detected PA amplitude on different THz excitation pulse widths is explored. First, the accumulative effect of EM energy for PA generation can be achieved when the temporal duration of the pulse is less than the minimum of the medium's thermal relaxation time $t_{thermal}=L^2/4D$ and stress relaxation time $t_{stress}=L/v_s{}^{12}$, where L is the characteristic size of the heated region, D is the thermal diffusion coefficient, and $v_s$ is the sound velocity in the medium. In this example, the thickness of the CNT-PDMS composite is approximately 30 μm. For the D and $v_s$, the maximum values of PDMS and water are taken for underestimation of the relaxation time, although it is believed that the main surrounding medium for the relaxation of CNT absorption is PDMS. Such estimation assures that the pulses with temporal duration less than 20 ns satisfy the accumulative effect of EM energy for PA generation. Quantitative calculations are then performed to clarify the response of detected PA amplitude with excitation by different pulse widths, from one picosecond to ten nanoseconds, at fixed energy per pulse, as shown in FIG. 11. The calculations are described in Chen, et al., "Low-noise small-size microring ultrasonic detectors for high-resolution photoacoustic imaging," *J. Biomed. Opt.*, 16, p. 056001 (2011), the relevant portions of which are expressly incorporated by reference. Thus, a calculated PADTH response with respect to excitation pulse widths is shown in FIG. 11. The calculation results of the response of normalized PA amplitude with various excitation pulse widths (1 ps to 1 ns) with fixed pulse energy is shown, which assumes that no sample damage occurs.

The composite transducer/absorber size of 30 μm, the bandwidth of 100 MHz of microring ultrasonic detectors, and sound propagation distance of 1 mm are considered in the calculation. It can be seen that the response is flat for pulse duration less than 2 ns, as long as sample damage is not produced. In other words, the PADTH rejects incoming radiation with time variation longer than tens of ns. This also shows the PADTH is suitable for a wide range of pulse widths.

The detected PA signal by the PADTH method of certain aspects of the present disclosure essentially gates the THz pulse excitation, thus rejecting continuous radiation, such as blackbody radiation. Thus, when they are used in THz pulse detection, the detection limit of the PADTH will not be limited by such background radiation. When using thermal detectors, the signal from background radiation can be reduced by modulation and lock-in techniques. However, due to the slow response time of most thermal detectors, only low modulation frequencies are allowed, which is not desirable for high SNR because noise spectral density is usually higher at low frequencies.

Example 4

In this example, the thermalization process taking place in the CNT-PDMS composite is investigated. As mentioned above, in certain embodiments, a 3D CNT-PDMS composite is formed by first growing CNTs to a thickness of no more than approximately 50 μm. Meanwhile, to maximize the THz absorption, the thickness of as-grown CNTs is not too thin. Thus, the thickness in this example of the as-grown CNTs is prepared at about 40 μm to about 50 μm. The as-grown CNT with a height or thickness of approximately 50 μm is sufficiently thick to collect THz energy. As for the final thickness of the CNT-PDMS composite, generally thinner is desirable, because too thick of a sample may result in unwanted acoustic attenuation in the composite. As noted above, the counterexample of thick sample of approximately 500 μm is shown in FIG. 3(a), where an unnecessary blank PDMS layer over the composite introduces excess acoustic attenuation. Thus, a polymer layer for the composite has an approximate 30 μm-thickness, because such thin free-standing film can still be handled without difficulty.

Based on a transmission measurement, it is estimated that the absorption of the 30-μm-thick composite is more than half at frequencies >1 THz. The thermalization process taking place in the CNT-PDMS composite is explored herein. After the THz energy is absorbed by the CNTs, the generated heat is transferred from CNTs to the surrounding PDMS within nanoseconds, resulting in a temperature rise of PDMS. The generated PA pressure is mainly contributed by the temperature rise and the thermoelastic effect of the PDMS. For a sufficiently short laser pulses, the initial pressure induced by the laser excitation is given by $p_0=\beta T/\kappa$, where β denotes the thermal coefficient of volume expansion; κ denotes the isothermal compressibility; T denotes the temperature rise. In this experiment, the measured pressure is approximately 700 Pa. Thus, it is estimated that the temperature rise in the composite is on the order of mK.

Example 5

Sensitivity of the detection of a PADTH device according to certain aspects of the present disclosure is further discussed herein. The noise-equivalent power (NEP) is one common figure of merit for conventional thermal THz detectors and characterizes their sensitivity. However, since the PADTH according to certain aspects of the present disclosure essentially detects each THz pulse, rather than the accumulated energy in a certain period (e.g., power) that is employed in other thermal detectors, the NEDE is more suitable for characterizing the PADTH. Specifically, the NEP is a universal standard for conventional thermal detectors for a variety of THz sources, including CW THz source and pulsed THz source with different PRF. Once the power of the THz source is same, they produce same SNR using different detectors with same NEPs at a given measurement time. In contrast, the relation between NEP (for 1-sec measurement time) and NEDE (for 1 pulse) of PADTH detection is NEP=NEDE×PRF$^{1/2}$, where NEP is proportional to PRF$^{1/2}$. That is, with the same PADTH system, different SNR will be obtained for different PRF of the pulsed THz source with same power at a given measurement time. Thus, NEP is not a universal standard to characterize the PADTH's sensitivity.

Although the PADTH according to certain aspects of the present disclosure and conventional thermal detectors are characterized using different figures of merit, they can be compared in some specific cases. For example, considering the THz source used in this experiment with pulse energy of 3.6 nJ and PRF of 500 Hz for 1-sec measurement time, the detection limit of pulse energy by the PADTH is 9.8 pJ [=(220 pJ)/sqrt(500)], while that by the commercial pyroelectric detector used in this experiment (NEP=1 nW/Hz$^{1/2}$) is 2 pJ [=(1 nW)/(500 Hz)]. In this case, they have similar performance in the detection limit. Thus, the PADTH device can be used as a practical THz detector. Moreover, some applications such as high-speed THz imaging, real-time alignment, and quantification of pulse energy fluctuation can only be achieved by the PADTH owing to its fast response time of approximately 0.1 μs, while the conventional pyroelectric detector has to wait approximately 0.2 sec for one measurement no matter how strong the THz source is. In certain variations, the PADTH device is able to detect each pulse of the pulsed THz source with PRF less than 10 MHz for high-speed applications. A comparison of performance metrics between PADTH and other thermal detectors is provided in Table 2.

From calculations of the signal amplitude for the composite material configured in the form of an acoustic lens, sensitivity can be further improved, for example, 10-20 times improvement in NEDE considering a focused THz spot size of 800 μm. A Q factor of polymer microring resonators to 10$^6$ has been achieved. Further enhancement of the Q factor is contemplated. Combining the two improvements, it is expected that more than 3 orders of magnitude improvement of PADTH sensitivity can potentially be achieved. That is, the PADTH devices according to certain variations of the present disclosure have potential to achieve a NEDE on the order of 0.1 pJ. The possibility for the microring detectors to be configured in arrays is another advantage of PADTH for THz imaging applications.

Benefited by the mechanism of transient and localized heating of the absorber, the rejection of continuous radiation from the ambient, and the optimization of the PA transmitter and the ultrasonic detector using the inventive PADTH technique, sensitive THz pulse detection has been demonstrated. The sensitivity and NEDE of approximately 220 pJ of one THz pulse is experimentally calibrated. The dependence of the converted PA amplitude on different pulse duration of THz excitation is illustrated, which shows a flat response for THz pulse duration less than 2 ns. Also, the ability for real-time detection with response time on the order of 0.1 μs is demonstrated. THz pulsed imaging using PADTH method has also been demonstrated. Note that a lower detection limit for the THz energy can be achieved with a corresponding increase in measurement time. The PADTH devices according to certain aspects of the present disclosure confer several advantages, including (1) room temperature and easy and low-cost operation, (2) small size, on-chip design for easy integration (3) fast response in 0.1 μs time scale, (4), relatively good sensitivity and NEDE, and (5) wide spectral response, offering great potential for various THz applications.

Unlike PZT transducers, the sensitivity of microring detectors is not limited by their sizes (typically 50-100 μm in diameter). The PA signal amplitude is proportional to excited light energy density (fluence). Due to the characteristic of long wavelength at THz frequencies, the smallest focal spot size is relatively large, for example approximately 1 mm, resulting in much lower fluence compared with the spot size of micrometer scale achieved at visible wavelength. One way to further improve the PADTH's efficiency

TABLE 2

Comparisons of an Embodiment of PADTH and other conventional thermal detectors

| Detector type | Response time (or modulation frequency) | Operation frequency (THz) | Noise-equivalent power (W/Hz$^{1/2}$) | Detection mechanism | |
|---|---|---|---|---|---|
| Conventional Bolometers* | 0.1 ms | ≤30 | 10$^{-14}$ | Electric resistance sensitive to temperature change | Time integration (i.e., power) |
| Conventional Pyroelectric detectors | 0.1 ms | ≤30 | 10$^{-9}$ | Spontaneous electric polarization susceptible to temperature change | |
| Conventional Golay cells | 0.05 s | ≤30 | 10$^{-9}$-10$^{-10}$ | Thermal expansion of the gas | |
| PADTH Embodiment of the present disclosure | 0.1 μs | at least ≥1.5 THz | 2.2 × 10$^{-10}$ J** | PA conversion (energy detection for pulse duration < 2 ns) | |

*operated at or below liquid helium temperature
**NEDE is used to characterize the PADTH sensitivity in accordance with certain aspects of the present disclosure is to further focus the generated acoustic pressure to an acoustic focal size of tens of micrometers by providing the THz absorbing material of the transducer in the form of an optoacoustic lens. FIG. 12(a) is a schematic showing an exemplary PADTH device 202 as part of a THz detection system 200 having improved sensitivity provided by use of an optoacoustic lens 210 in the system. The system 200 includes a source of radiation 212 to create focused THz radiation pulses 220 like those described above. The radiation pulses 220 are directed towards the optoacoustic lens 210 that serves as the transducer.

The optoacoustic lens 210 thus converts THz energy in the form of THz radiation pulses 220 into pressure waves forming a focused acoustic beam 230 via the photoacoustic effect. The optoacoustic lens 210 serves to further focus generated acoustic pressure to an acoustic focal size on the order of tens of micrometers (e.g., from ≥ about 10 μm to ≤ to about 100 μm). The optoacoustic lens 210 may be a concave lens 206 having a THz absorbing material 208 formed thereon as a layer. In certain variations, the THz absorbing material 208 may be a nanocomposite comprises a plurality of THz radiation absorbing particles and a polymer, such as a CNT-PDMS composite. The focused acoustic beam 230 is directed towards an acoustic sensor 232 that includes a microring resonator device configured to receive the focused acoustic beam 230 produced by the photoacoustic transducer in the form of the optoacoustic lens 210.

The PADTH's efficiency can be further improved by focusing the generated acoustic pressure to an acoustic focal size of tens of micrometers by configuring the composite in the form of an optoacoustic lens. The optoacoustic lens can fully utilize the advantage of small element size and high sensitivity of the microring detector for efficient PADTH detection. FIG. 12(b) shows two different sizes of THz transducer optoacoustic lenses formed having a CNT-PDMS composite layer as the THz absorbing material according to certain aspects of the present disclosure. The lenses are both plano-concave fused silica lenses. The lens on the left has a diameter of 6 mm and the lens on the right has a diameter of 12 mm. The optoacoustic lenses are formed by first growing CNTs on the surface of the concave side of the plano-concave fused silica lenses and then overcoating the CNTs with PDMS to form the composite layer. The lenses are used for laser-generated focused ultrasound. Such CNT-PDMS optoacoustic lenses can thus focus the green-laser-excited pressure wave to a tight focal spot.

In certain variations, a system including THz modulation and reconfigurable THz quasi-optical component using photo-induced pattern on semi-insulating silicon are contemplated. This allows THz imaging by using a single PADTH element in the system in accordance with the present teachings. For example, a reconfigurable semi-optical terahertz (THz) radiation imaging system may comprise a terahertz (THz) radiation PADTH detection device as are described above. The system may also include a source of pulsed terahertz (THz) radiation, a silicon wafer, and a source of light configured to direct a reconfigurable photopattern onto the silicon wafer. The photoinduced reconfigurable patterns formed on the silicon wafer serve to produce free carrier concentrations and thus shift the plasmon frequency, which changes the THz absorption property of the silicon wafer. An object to be imaged may be disposed between the source of pulsed THz radiation and the silicon wafer. The terahertz (THz) radiation PADTH detection device is capable of imaging the object. For example, the light source may be a digital light processing projector. By doing a raster scan of the DLP projector, a THz image can be obtained. Other conventional imaging and optic components and devices may also be present in such an imaging system, including a computer processing unit.

An exemplary simple THz imaging system 300 using a light-activated spatial THz modulator along with a PADTH device employed for THz detection shown in FIGS. 13(a)-13(b). The basic principle uses photo-induced reconfigurable patterns on a silicon wafer to produce higher free carrier concentrations therefore shifting the plasmon frequency, which in turn changes the THz absorption property of the silicon. In the system 300, a commercially-available digital light processing (DLP) projector 310 can be used to create light patterns on a silicon wafer 320. The system includes the DLP projector 310 that projects through a projection lens 312 and then through an ITO coated glass element 314. A source of radiation (not shown, but like those described above) passes through an optical chopper 316 to create THz radiation pulses 318 like those 312 described above. The radiation pulses 318 are directed towards an object 322 to be imaged and then onto a parabolic mirror component 324. The THz beam is then directed towards the semi-insulating silicon wafer 320.

In the system 300, the DLP projector 310 projects light through a projection lens 312 and then through an ITO coated glass element 314. The DLP projector 310 thus creates one or more light patterns 340 on the silicon wafer 320 by projecting light 350 in a photopattern towards a first side 342 of the silicon wafer 320 as shown in FIG. 13(b). Meanwhile, a second side 344 of the silicon wafer 320 receives the pulsed THz radiation 318 that is transmitted through the silicon wafer 320 and out the first side 342. As noted above, the light patterns 340 on silicon wafer 320 produce higher free carrier concentrations and shifts the plasmon frequency, which changes the THz absorption property of the silicon.

By doing a raster scan of the DLP projector, THz images can be obtained using only a single-element PADTH detector device 330, although multiple PADTH detector devices may also be used. The PADTH detector device 330 is used to detect the modulated THz pulse radiation. The PADTH detector device 330 may be any of those described previously above. The PADTH detector device includes a photoacoustic transducer configured to receive a pulse of terahertz (THz) radiation that produces an acoustic wave in response to receiving the pulse of THz radiation and an acoustic sensor configured to receive the acoustic wave produced by the photoacoustic transducer. An image of the object 322 may thus be detected in the PADTH detector device 330.

The fast spatial intensity modulation brought by THz imaging systems and fast response time of the PADTH device 330 provide the ability to realize real-time THz pulsed imaging. Providing a plurality of elements to form an array of PADTH devices may also increase the image acquisition speed. Another advantage is that an arrayed microring detector can be constructed with element spacing of less than or equal to about 100 μm, where each microring detector can be addressed by a single bus waveguide by using wavelength division multiplexing scheme. The possibility for the microring detectors to be configured in arrays is useful for THz imaging applications.

In other aspects, the present disclosure contemplates systems for THz communication. As an extension of microwave and millimeter wave bands, THz frequency offers greater communications bandwidth than is available at microwave frequencies. Especially for satellite-to-satellite communications, atmospheric absorption is not a problem. Also indoor wireless communications with THz may provide multiple data channels with gigabit per second or higher. Atmospheric transmission windows may allow application of THz for short-range tactical communication. The beamlike properties of THz emission reduce the ability of interception of these transmissions by distant third parties. As the PADTH detection devices have the ability to detect pulsed and modulated THz energy, they are particularly well suited for communication systems. Further, such PADTH detection devices are useful in communication systems in view of their ability to detect polarized THz radiation and/or to determine a polarization state of the THz signals received. Because the photoacoustic THz detector technology according to the present disclosure works for pulsed THz radiation, such technology is naturally fitted for use in THz communication by detecting nanosecond pulses, e.g., modulation frequency on the order of GHz.

Thus, the present disclosure contemplates a terahertz (THz) radiation communication system that may include a transmitter for creating pulsed and modulated THz communication signals. The communication system may also include a receiver incorporating the terahertz (THz) radiation PADTH detection device according to any of the variations described herein for detecting the pulsed THz communication signals. Other conventional communication components and devices may also be present in such a communication system.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A terahertz radiation detection device comprising:
    a photoacoustic transducer configured to receive a pulse of terahertz (THz) radiation, wherein the photoacoustic transducer comprises a THz absorbing material in a solid, semi-solid, or liquid phase and the photoacoustic transducer produces an acoustic wave in response to receiving the pulse of THz radiation; and
    an acoustic sensor configured to receive the acoustic wave produced by the photoacoustic transducer.

2. The device of claim 1, wherein the THz absorbing material comprises a composite material having a polymeric matrix material and a plurality of radiation absorbing particles selected from the group consisting of: carbon nanotubes, graphene oxide, and combinations thereof distributed in the polymeric matrix material.

3. The device of claim 1, wherein the acoustic wave is an ultrasonic wave having a frequency of greater than or equal to about 20 kHz.

4. The device of claim 1, wherein the THz absorbing material comprises a dielectric doped semiconductor material or a metamaterial structure comprising a metallic structure and a dielectric material.

5. The device of claim 1, wherein the acoustic sensor comprises a polymer microring resonator or a piezoelectric based acoustic detector and the device further comprises a coupling medium disposed between the photoacoustic transducer and the acoustic sensor.

6. The device of claim 1, wherein the THz absorbing materials are patterned into an array of stripes providing anisotropic absorption of the pulse of THz radiation.

7. A terahertz (THz) radiation communication system comprising:
    a transmitter for creating modulated and pulsed THz communication signals; and
    a receiver incorporating the terahertz (THz) radiation detection device of claim 1 for detecting the pulsed THz communication signals.

8. A reconfigurable terahertz (THz) radiation imaging system comprising:
    the terahertz (THz) radiation detection device of claim 1;
    a source of pulsed terahertz (THz) radiation;
    a silicon wafer;
    a source of light configured to direct a reconfigurable photopattern onto the silicon wafer; and
    an object to be imaged that is disposed between the source of pulsed THz radiation and the silicon wafer; wherein the terahertz (THz) radiation detection device is capable of imaging the object.

9. The device of claim 2, wherein the plurality of radiation absorbing particles comprises carbon nanotubes grown as a carbon nanotube forest and having the polymeric matrix material distributed therein.

10. The device of claim 2, wherein the polymeric matrix material is an elastomer comprising polydimethylsiloxane.

11. The device of claim 2, wherein the composite material has a thickness of less than or equal to about 50 μm.

12. The device of claim 2, wherein the composite material has a shape of an acoustic lens such that the acoustic wave produced by the photoacoustic transducer is focused to the acoustic sensor.

13. The device of claim 9, wherein an average diameter of each carbon nanotube is greater than or equal to about 5 nm to less than or equal to about 25 nm, an average height of each carbon nanotube is greater than or equal to about 1 μm to less than or equal to about 500 μm and spacing between adjacent carbon nanotubes is greater than or equal to about 25 nm to less than or equal to about 250 nm.

14. A method for detecting terahertz radiation comprising:
    generating an acoustic wave within a photoacoustic transducer by receiving a pulse of terahertz (THz) radiation, wherein the photoacoustic transducer comprises a THz absorbing material in a solid, semi-solid, or liquid phase; and
    detecting the acoustic wave with an acoustic sensor.

15. The method of claim 14, wherein the generating and the detecting occur in less than or equal to about 1 μs.

16. The method of claim 14, wherein the generating and the detecting occur in less than or equal to about 0.01 μs.

17. The method of claim 14, wherein the detecting occurs in real-time.

18. The method of claim 14, wherein the acoustic wave is an ultrasonic wave having a frequency of greater than or equal to about 20 kHz.

19. The method of claim 14, wherein the acoustic wave is an ultrasonic wave having a frequency of greater than or equal to about 10 MHz and an output pressure of greater than or equal to about 10 Pa.

20. The method of claim 14, wherein the THz absorbing material comprises a composite material having a polymeric matrix material and a plurality of radiation absorbing particles distributed in the polymeric matrix material.

21. A terahertz radiation detection device comprising:
    a photoacoustic transducer configured to receive a pulse of terahertz (THz) radiation, wherein the photoacoustic transducer produces an acoustic wave in response to receiving the pulse of THz radiation and the photoacoustic transducer comprises a composite material having an elastomer polymeric matrix material and a plurality of THz absorbing particles selected from the group consisting of: carbon nanotubes, graphene oxide, and combinations thereof distributed in the elastomer polymeric matrix material; and an acoustic sensor configured to receive the acoustic wave produced by the photoacoustic transducer.

\* \* \* \* \*